(12) United States Patent
Boveja et al.

(10) Patent No.: US 9,393,071 B1
(45) Date of Patent: *Jul. 19, 2016

(54) METHODS AND SYSTEMS OF TEMPERATURE BASED ALARMS AND/OR AUTOMATIC INTERRUPT (SHUTOFF) DURING A CARDIAC ABLATION PROCEDURE

(71) Applicants: Birinder R. Boveja, Greenfield, WI (US); Mohammad MasoudiMotlagh, Milwaukee, WI (US); Angely Widhany, Greenfield, WI (US)

(72) Inventors: Birinder R. Boveja, Greenfield, WI (US); Mohammad MasoudiMotlagh, Milwaukee, WI (US); Angely Widhany, Greenfield, WI (US)

(73) Assignee: ABL TECHNOLOGIES, LLC, Wauwatzsa, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,445

(22) Filed: May 11, 2015

Related U.S. Application Data

(63) Continuation-in-part of application No. 13/718,284, filed on Dec. 18, 2012, now Pat. No. 9,033,968.

(51) Int. Cl.
| | |
|---|---|
| *A61B 18/14* | (2006.01) |
| *A61B 18/02* | (2006.01) |
| *A61B 18/00* | (2006.01) |
| *A61B 19/00* | (2006.01) |

(52) U.S. Cl.
CPC ............. *A61B 18/1492* (2013.01); *A61B 18/02* (2013.01); *A61B 2018/00351* (2013.01); *A61B 2018/00577* (2013.01); *A61B 2018/00672* (2013.01); *A61B 2018/00678* (2013.01); *A61B 2018/00708* (2013.01); *A61B 2018/00714* (2013.01); *A61B 2018/00797* (2013.01); *A61B 2018/00815* (2013.01); *A61B 2018/00821* (2013.01); *A61B 2018/00898* (2013.01); *A61B 2019/4836* (2013.01)

(58) Field of Classification Search
CPC ........ A61B 5/01; A61B 5/4233; A61B 1/273; A61B 18/1492; A61B 2018/00577; A61B 2018/00636; A61B 2018/00797; A61B 2018/00791
See application file for complete search history.

(56) References Cited

U.S. PATENT DOCUMENTS

| | | | |
|---|---|---|---|
| 5,348,554 A | 9/1994 | Imran et al. | |
| 7,819,817 B2 | 10/2010 | Rahn | |
| 8,224,422 B2 | 7/2012 | Mottola | |
| 8,271,095 B2 | 9/2012 | O'Sullivan | |
| 8,273,016 B2 | 9/2012 | O'Sullivan | |
| 8,355,801 B2 | 1/2013 | O'Sullivan | |
| 8,512,387 B2 * | 8/2013 | Fishel | A61B 18/1492 128/898 |
| 2007/0066968 A1 * | 3/2007 | Rahn | A61B 5/01 606/27 |
| 2014/0012155 A1 | 1/2014 | Flaherty et al. | |

* cited by examiner

*Primary Examiner* — Robert N Wieland

(57) ABSTRACT

A method and system for increasing safety of cardiac ablation procedures comprises a computer based system that monitors the esophageal temperature. The esophageal temperature is monitored utilizing an esophageal probe which may have any number of temperature sensing members. The esophageal probe may also have pre-formed shape. During atrial fibrillation ablations, based on a pre-determined increase in esophageal temperature (from any thermistor), the computer based system activates different levels of alarm(s), and/or initiates ablation energy interrupt based on pre-defined programmed values. The method and system may also be used during cryoablations.

20 Claims, 29 Drawing Sheets

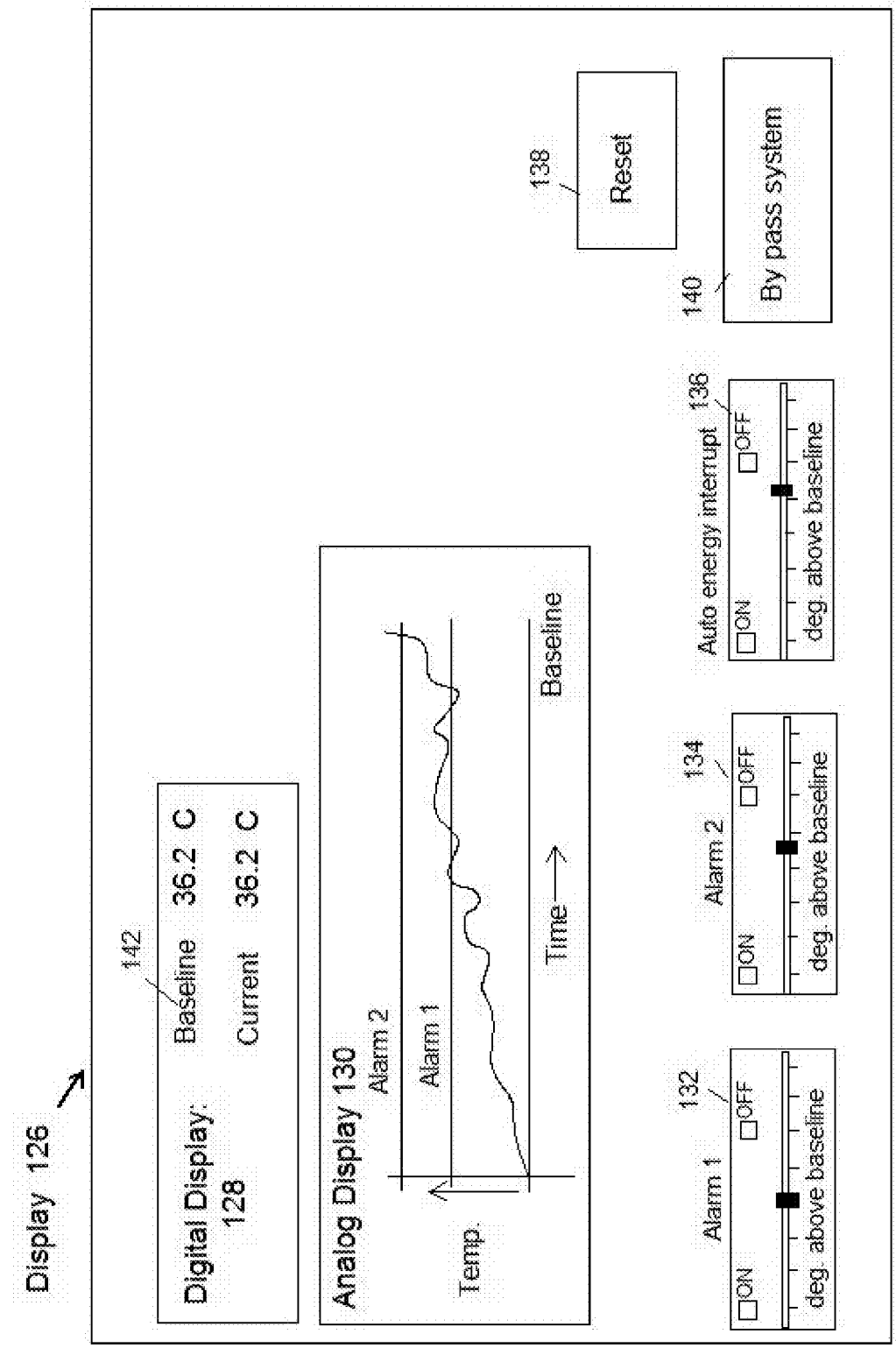

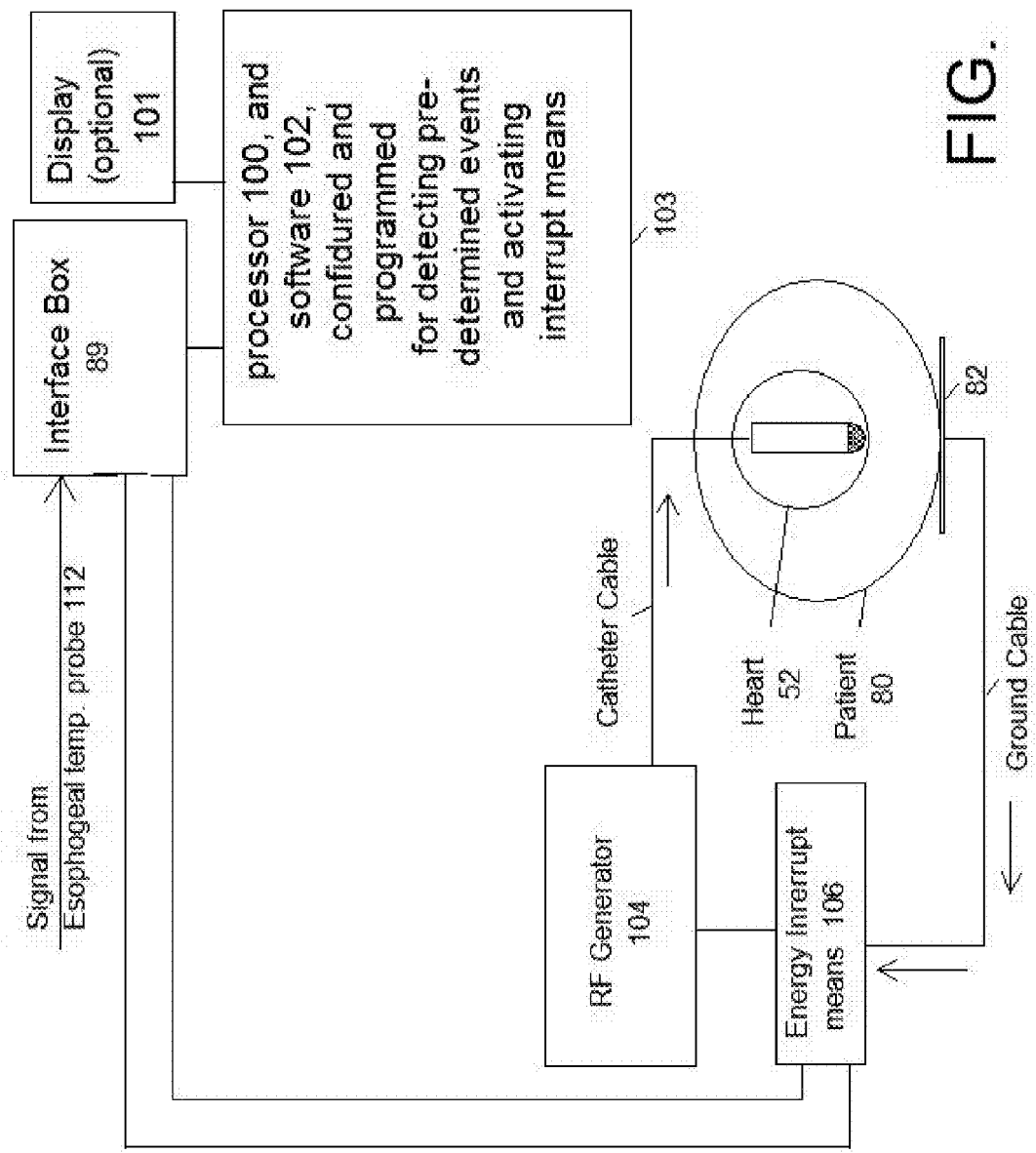

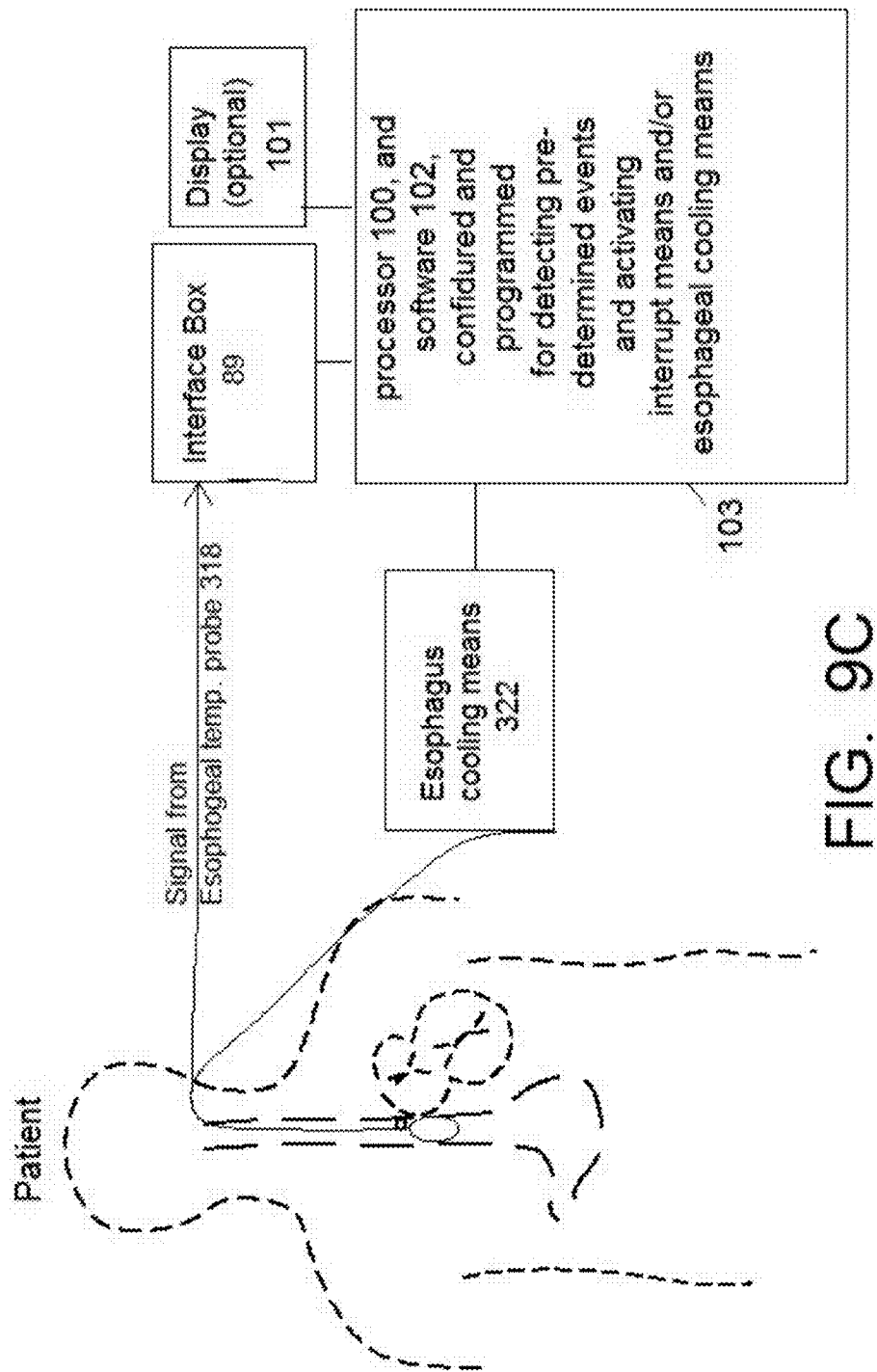

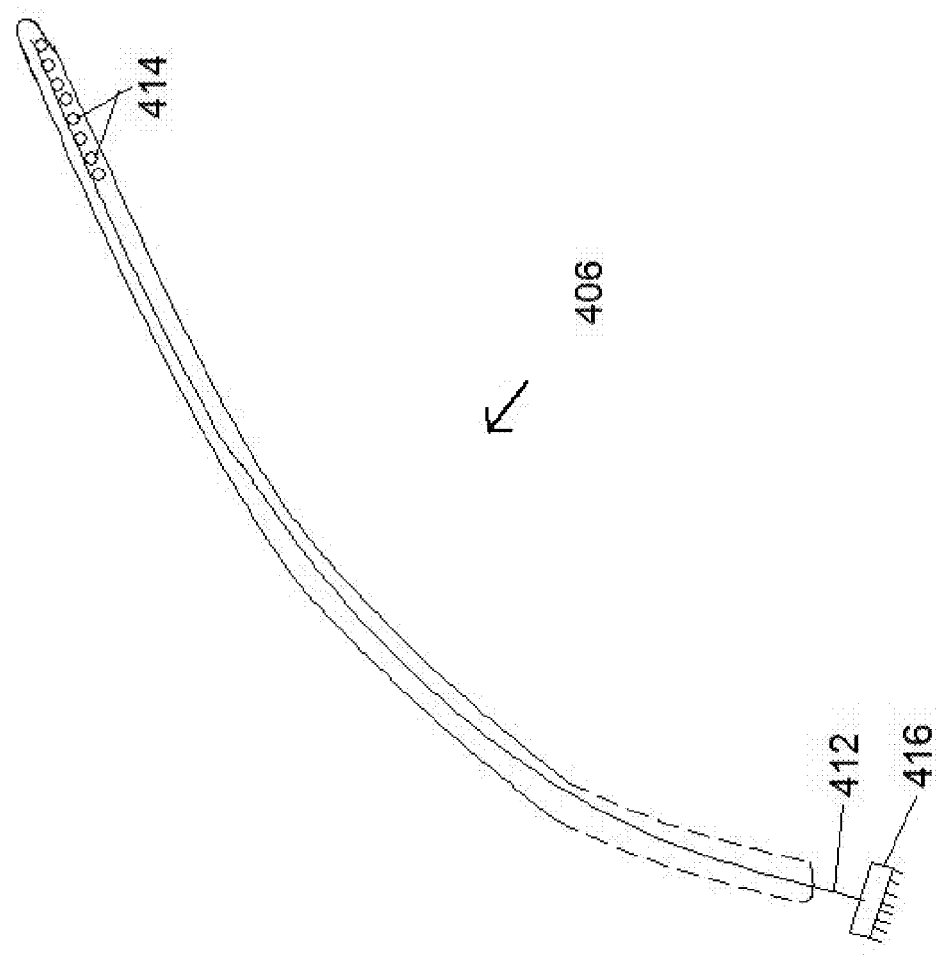

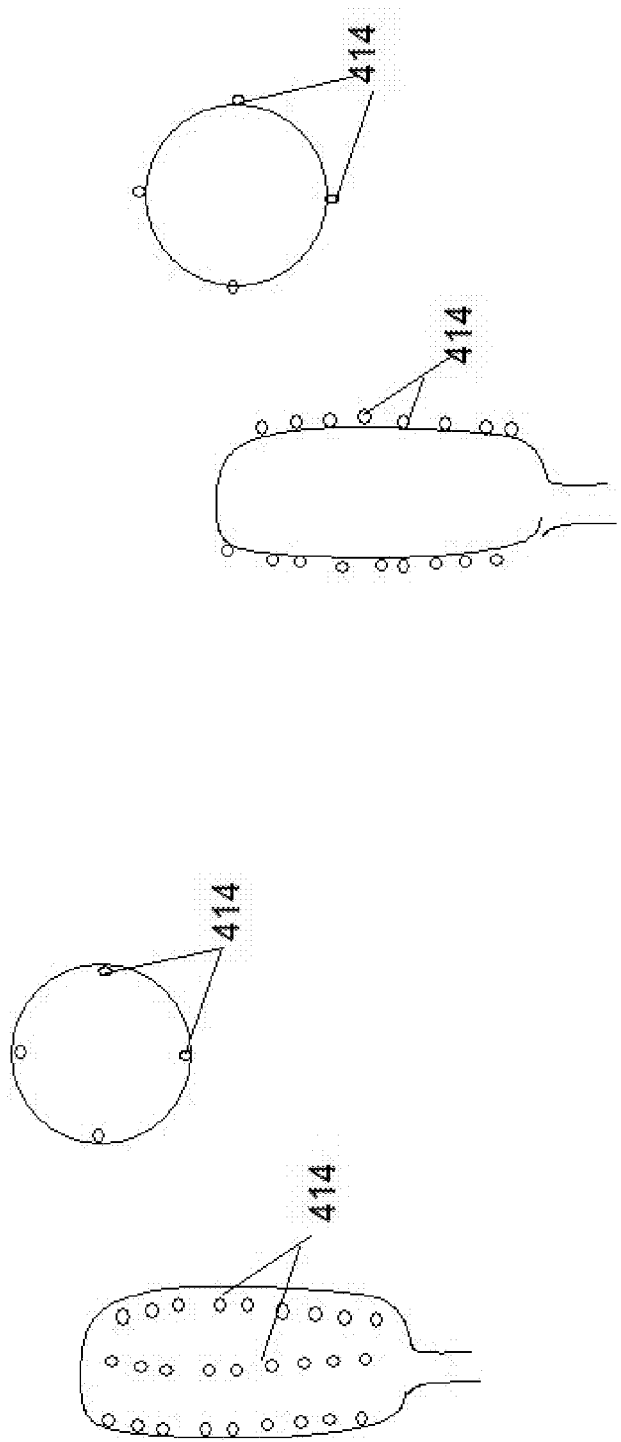

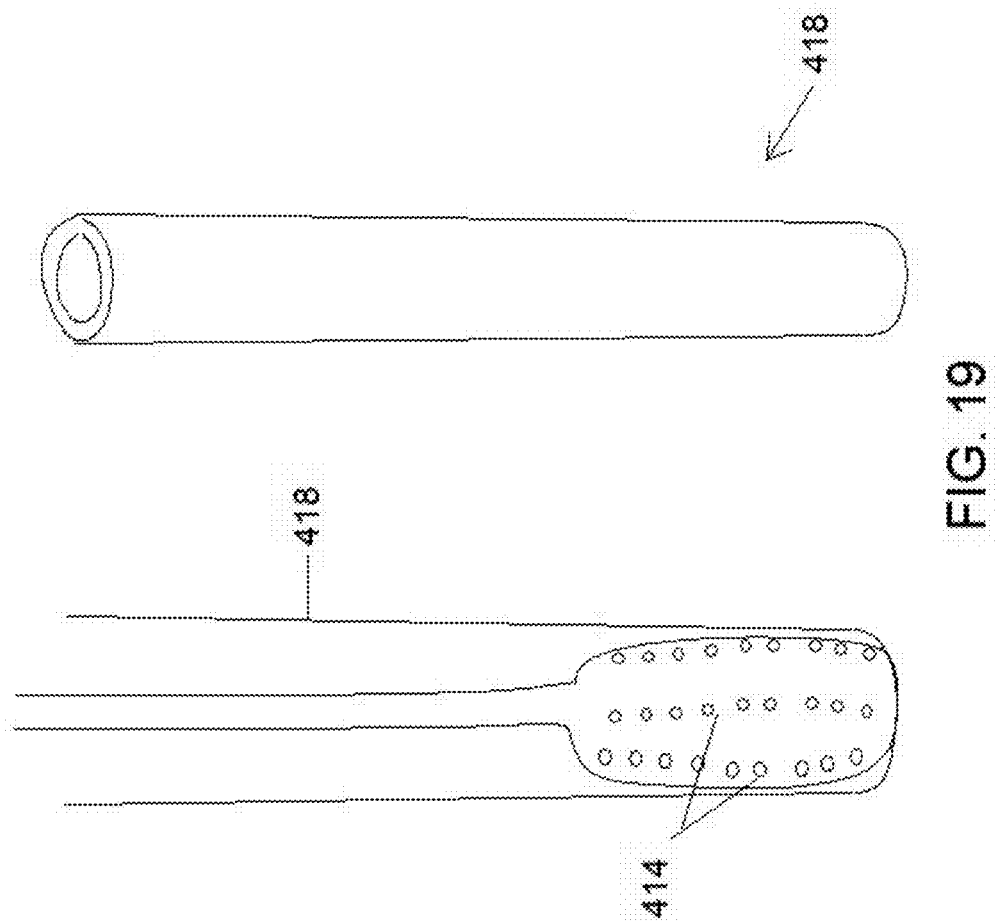

METHODS AND SYSTEMS OF TEMPERATURE BASED ALARMS AND/OR AUTOMATIC INTERRUPT (SHUTOFF) DURING A CARDIAC ABLATION PROCEDURE

This application is a Continuation-in-part (CIP) of U.S. application Ser. No. 13/718,284 now U.S. Pat. No. 9,033,968. U.S. patent application Ser. No. 13/718,284 also claims priority date of U.S. Provisional Application No. 61/630,771 filed on Dec. 19, 2011 which is hereby incorporated by reference in its entirety.

FIELD OF DISCLOSURE

The present disclosure relates to atrial fibrillation ablations, more specifically to method and system for increasing safety of atrial fibrillation procedures by monitoring esophageal temperature, and setting levels for alarms(s) and/or energy delivery interrupt.

BACKGROUND

Atrial fibrillation (AF) is the most prevalent cardiac arrhythmia. It affects 1% to 2% of the general population with an important increase in incidence with age. In the United States it is estimated that over 5 million people have atrial fibrillation, and because of our aging population the prevalence of this arrhythmia will increase significantly over the next decade.

Atrial fibrillation is associated with increased morbidity and mortality, and in particular, a general decrease in quality of life for those afflicted with atrial fibrillation. AF can also cause tachycardia mediated cardiomyopathy or worsening of pre-existing heart failure. Moreover, AF is known to increase the mortality risk 1.5-2 fold with the risk for stroke five-fold. Patients are at an increased risk of stroke unless they are treated adequately with anticoagulants. Anticoagulant treatment however, increases the patient's risk of bleeding, which carries with it is own set of dangers. Medications currently available for treating atrial fibrillation have proven to be only moderately effective in decreasing the incidence of recurrent atrial fibrillation, and these medications do not decrease the patient's risk of having a stroke.

One method of treating atrial fibrillation has been to perform ablation of selected areas of the left atrium. There is strong evidence to suggest that ablating these areas of the left atrium serves to cure or prevent further incidences of atrial fibrillation, which thereby has shown to reduce the risk of stroke and reduce the necessity of anticoagulant therapy. Typically, ablation of this type is carried out via an intravascular catheter using radiofrequency or microwave energy to cause thermal changes to the selected parts of the left atrial tissue.

Besides having a good safety profile, catheter ablation therapy for AF has proved effective in establishing and maintaining sinus rhythm. Ablation for atrial fibrillation is now the most commonly performed procedure in most laboratories.

The posterior wall of the left atrium is particularly targeted for ablation because the pulmonary veins enter the atrium at this area of the left atrium, encircling the pulmonary veins with continuous rings of lesions in this procedure. The esophagus may however be, in a position so as to overlie one or more of these circles, thereby making the desired encirclement difficult or impossible.

A significant and lethal complication of atrial fibrillation ablation is the accidental creation of an atrial esophageal fistula following the development of lesions on the posterior wall of the left atrium. Because the esophagus is generally in close position to the posterior wall of the left atrial, thermal injury may be communicated to the esophageal wall resulting in disruption of the wall and formation of the atrial esophageal fistula. Thermal esophageal lesions are believed to be precursors of fistula formation. Post ablation esophageal wall changes (erosion or ulceration) are reported to occur in up to 47% of patients. Real time temperature monitoring can detect rapid esophageal heating during radiofrequency ablation.

Although the pathophysiology of left atrial-esophageal (LA-Eso) fistula formation is not fully understood, it is clear that thermal injury to the esophagus during ablation of the LA posterior wall plays a crucial role in triggering the cascade of events that eventually result in the development of LA-Eso fistula.

Currently, the most commonly used clinical strategy to minimize esophageal thermal injury during AF ablation involves limiting the magnitude of power 25 to 35 W, as well as the duration (<30 s), of RF applications placed along the posterior wall of the LA. A major limitation of this approach is that it fails to account for the variability in the thickness of the posterior LA wall and the presence of peri-esophageal connective tissue—important determinants of esophageal heating. Thus, empirically limiting the power and duration of RF applications may be insufficient to prevent esophageal thermal injury in all patients. RF power delivery during AF ablation, guided by luminal esophageal temperature (LET) monitoring is associated with less frequent esophageal injury compared with a strategy of power limitation alone.

Also, it is known that successful atrial fibrillation ablation may require the introduction of lesions near the location of the inferior right pulmonary vein, which is located in close proximity to the phrenic nerve. Thus, it has become more common for accidental injury to the phrenic nerve to occur. The phrenic nerve is responsible for operation of the diaphragm, and thus, injury to the phrenic nerve can be quite catastrophic.

Luminal esophageal temperature (LET) monitoring is the most common strategy to minimize esophageal injury during atrial fibrillation (AF) ablation procedures. The esophageal probe may have one thermistor, or the esophageal probe may have multiple sensors on the body of the probe for measuring temperature from a length of the esophagus.

In addition to the foregoing, fractionated electrograms and vagal plexi are also frequently present on the posterior wall of the left atrium. These are also common targets of atrial fibrillation ablation. Again, the location of the esophagus may hinder application of this sufficient energy to successfully ablate enough energy of the left atrium to prevent recurrence of atrial fibrillation.

Since esophageal injury during RF ablation in the left atrium is thermal injury, and because of the need for preventing injury to the esophagus, there is a real need for a method and system for,
a) activating various levels of alarms based on esophageal temperature monitoring,
b) cooling the esophagus, and/or
c) automatically interrupting the energy delivery of the ablation circuit,
whenever the esophageal temperature reaches a predetermined critical level.

SUMMARY OF THE DISCLOSURE

The current disclosure discloses novel methods and system for increasing safety of atrial fibrillation ablations by monitoring and interrupting energy delivery of ablation procedure, based on increases in the esophageal temperature.

The method and system of this disclosure comprises a computer with software configured and programmed to set one or more alarms and/or computer based interrupt (shut-off) based on pre-selected levels during a cardiac ablation procedure, more specifically an atrial fibrillation procedure. Such levels can be, but not limited to, elevation in temperature level(s), or time duration of such elevation of temperature levels. The physician may select the level(s) or settings of one or more variables to suit individual patient needs. The method is configured to either set off alarm(s) or shut off the energy for the procedure or both. The baseline temperature, elevation in temperature level(s), or time duration or delay of such elevation of temperature levels have a range for the physician to select from. The range for duration may be from milliseconds to several seconds.

Accordingly, one objective of the disclosure is for a computer to monitor esophageal temperature and sound different levels of alarms or interrupt energy delivery based on pre-determined (threshold) levels of increases in the esophageal temperature.

In one aspect of the disclosure, when esophageal temperature increases above a first level predetermined threshold, an audio alarm is activated.

In another aspect of the disclosure, when esophageal temperature increases above a first level of predetermined threshold, an audio and visual alarm is activated.

In another aspect of the disclosure, when esophageal temperature increases above a second level predetermined threshold, a higher level of audio alarm is activated.

In another aspect of the disclosure, the predetermined event may be an increased level of esophageal temperature.

In another aspect of the disclosure, the predetermined event may be the rate of change of esophageal temperature.

In another aspect of the disclosure, the esophageal probe may comprise ten temperature sensors.

In another aspect of the disclosure, the esophageal probe may comprise 12 temperature sensors.

In another aspect of the disclosure, the esophageal probe may comprise one temperature sensor.

In another aspect of the disclosure, the esophageal probe may comprise any number of temperature sensors.

In another aspect of the disclosure, the esophageal probe may comprise thermistor sensors.

In another aspect of the disclosure, the esophageal probe may comprise thermocouple sensors.

In another aspect of the disclosure, the esophageal probe may have a body which straight in shape.

In another aspect of the disclosure, the esophageal probe may have a body which has a preformed shape.

In another aspect of the disclosure, the esophageal probe may have a body which has a preformed shape and can be straightened with a straight stylet.

In another aspect of the disclosure, when esophageal temperature increases above a second level predetermined threshold, a higher level of audio and visual alarm is activated.

In another aspect of the disclosure, when esophageal temperature increases above a first level of predetermined threshold, a siren is activated.

In another aspect of the disclosure, when esophageal temperature increases above a second level predetermined threshold, a higher level of a siren is activated.

In another aspect of the disclosure, when esophageal temperature increases above a predetermined threshold, the ablation energy to the heart tissue is interrupted.

In another aspect of the disclosure, the ablation energy to the heart tissue is interrupted based on increase in temperature and time duration of elevated temperature.

In one embodiment, the computer logic for esophageal temperature monitoring and corresponding alarms and interrupt logic is in a stand-alone computer in parallel to the patient monitoring system.

In another embodiment, the computer logic for esophageal temperature monitoring and corresponding alarms and/or interrupt logic is in a stand-alone computer where the esophageal signals to the stand-alone computer are obtained from the patient monitoring system.

In another embodiment, the computer logic for esophageal temperature monitoring and corresponding alarms and interrupt logic is in a stand-alone computer used independently of the patient monitoring system.

In another embodiment, the computer logic for esophageal temperature monitoring and corresponding alarms and interrupt logic and circuitry is incorporated within the patient monitoring system.

In another embodiment, the computer logic for esophageal temperature monitoring and corresponding alarms and interrupt logic and circuitry is incorporated within a 2-D or 3-D mapping system.

In another embodiment, the computer logic for esophageal temperature monitoring and corresponding alarms and interrupt logic and circuitry is incorporated within the ablation generator system.

In another aspect of the procedure, a method of eliminating/minimizing esophageal temperature related injury during atrial fibrillation cardiac ablation procedure is provided.

In another aspect of the disclosure, esophageal injury during ablation is minimized by cooling the esophagus, if the esophageal temperature increases.

In another aspect of the disclosure, the esophagus is cooled by cold saline which is brought into a balloon adapted to in the esophagus.

In another aspect of the disclosure, the cooling of the esophagus is done using gases.

In another aspect of the disclosure, cooling of the esophagus is done with in combination with alarms.

In another aspect of the disclosure, cooling of the esophagus is done with in combination with ablation energy interrupt.

Various other features, objects and advantages of the disclosure will be made apparent from the following description taken together with the drawings.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIG. 8B shows an example of graphical display and graphical interface of the concept with adjustable time delay.

FIG. 9A depicts schematically the overall concept of the system, with the circuit interrupt in the ground loop portion of the circuit.

FIG. 9C depicts the embodiment where the cooling means comprises a saline bag filled with cold saline that can be used for cooling the esophagus.

FIG. 16 is one embodiment of an esophageal probe with multiple sensors (thermistors), which is straight in shape.

FIGS. 18A and 18B show two embodiments where multiple sensors are on a inflatable apparatus. In FIG. 18A, the sensors are covered in a sheath or membrane. In FIG. 18B the sensors on an inflatable apparatus are exposed FIG. 19 depicts an esophageal probe with multiple sensors which is encased in a sheath or membrane.

DETAILED DESCRIPTION OF THE DISCLOSURE

The following description is of the best mode presently contemplated for carrying out the disclosure. This description is not to be taken in a limiting sense, but is made merely for the purpose of describing the general principles of the disclosure. The scope of the disclosure should be determined with reference to the claims.

Figure 1:
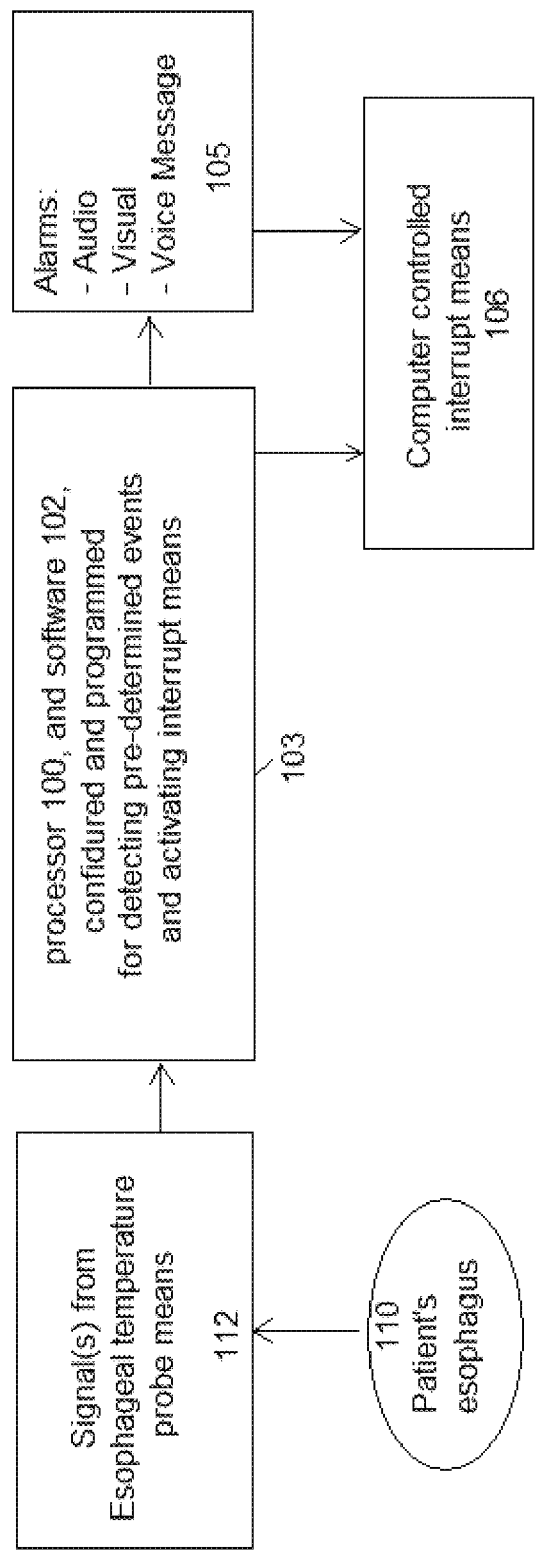
FIG. 1 is a block diagram of the concept of alarms and computer controlled interrupt based on esophageal temperature for atrial fibrillation ablations.

This disclosure is targeted to preventing or minimizing thermal injury to the esophagus or the vagus nerve(s) during ablation in the atrium, for treatment of atrial fibrillation. Accordingly, as shown in conjunction with FIG. 1 signals are typically and routinely recorded from an esophageal temperature probe 112 which is in a patient's esophagus 110.

The temperature probe may comprise a single or multiple thermisters. The multiple thermister probe may comprise any number of thermisters. In one preferred embodiment, the temperature probe may have ten thermistors. In other embodiments the probe the probe may have any number of thermisters. The goal is to cover the whole esophageal region, which could correspond to the left atrium. Another goal is that the coverage is large enough so the physician shouldn't have to move the esophageal probe during the procedure.

The temperature information is typically processed by a computer 103 comprising a processor 100 with algorithms 102 for pre-determined events, and displayed on a patient monitor which may be a stand-alone patient monitor or part of an anesthesia monitoring setup, or a cardiac recoding/monitoring system. During an atrial fibrillation ablation procedure this monitoring is typically done by an anesthesiologist, a nurse or an electrophysiologist performing this procedure. In the method and system of this disclosure, various levels of alarms and controls are incorporated within the monitoring system, such that at a programmable level there is an alarm indication that the temperature on the esophageal probe 112 has increased by a pre-determined level selected by the physician. This is shown in blocks 103 and 105 in FIG. 1. A second level(s) of alarms may also be established, indicating a further level of increase at the esophageal temperature probe. Finally, upon reaching a higher predetermined level of temperature increase, the computer may activate an interrupt means which may be a relay switch 106 or any other types of circuit breakers without limitation, which interrupts the energy delivery to the ablation circuit. At that point the physician either re-positions the catheter to another position in the atrium which is further away from the esophagus or waits for the temperature in the esophageal probe to come back down before resuming the ablation at that point.

Figure 2A:
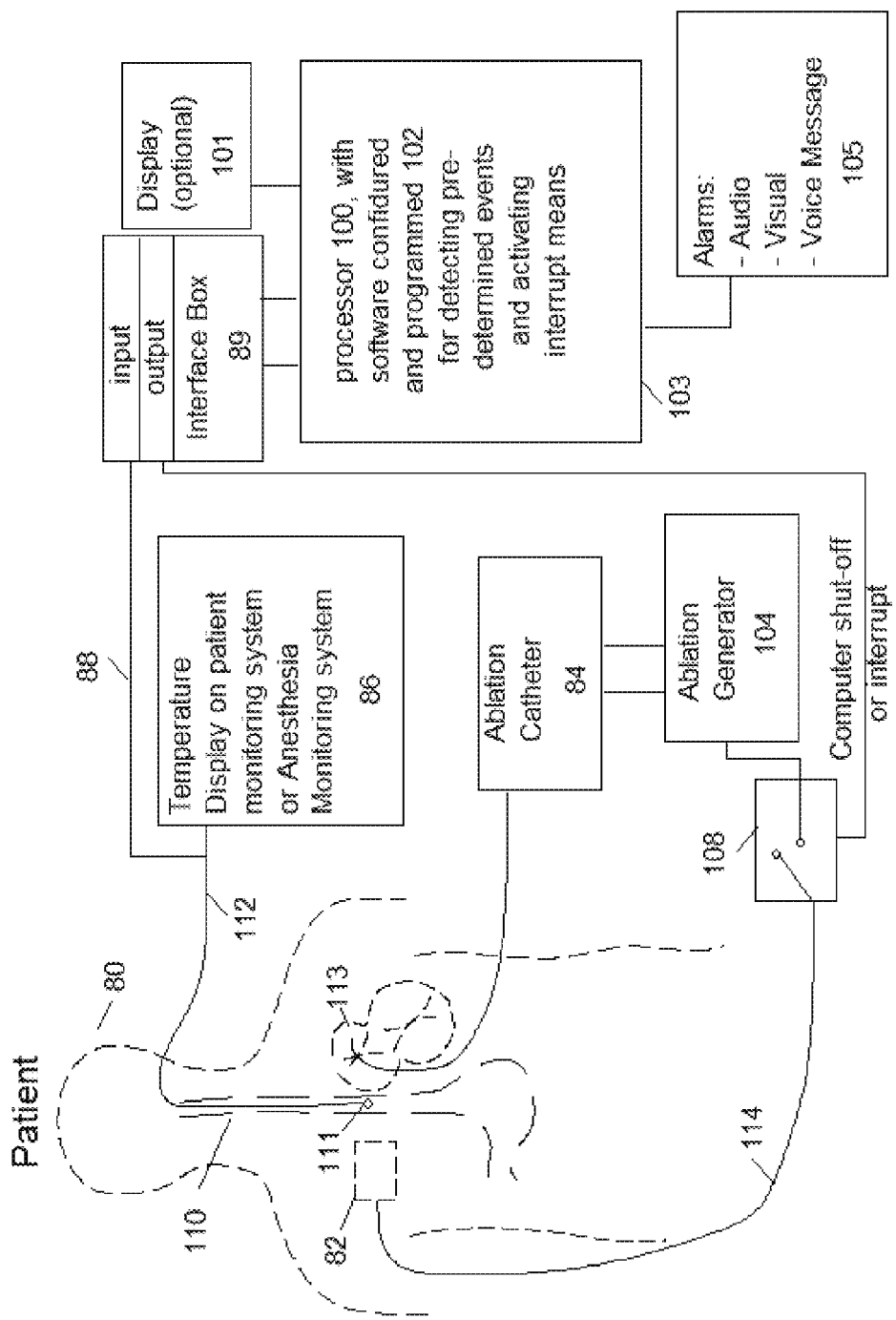
FIG. 2A depicts a general setup of the concept where the esophageal signals from the patient are split and slaved into another computer for monitoring, analyzing and interrupting atrial fibrillation ablation procedure.

This concept and various embodiments are described below in conjunction with FIGS. 2A-7. Shown in FIG. 2A is a schematic block diagram of one preferred embodiment of the disclosure. As shown in the figure an esophageal probe 112 is placed in the patient 80, such that the temperature probe 111 (usually a thermistor or a thermocouple) is in the esophagus 110 at the level of the left atrium 113, preferably at the level of the tip of the ablation catheter, and generally close to the ablation catheter which is in the left atrium 113.

In one embodiment the signal from the esophageal probe 112 is spilt or the signal is slaved 88 into an interface box 89 such that the information can be analyzed by a computer of the patient monitoring system 86, which is typically observed and monitored visually by the anesthesiologist or a nurse, and an additional computer 103 comprising processor 100 and algorithms 102 (software which is configured and programmed as described in the disclosure). In this disclosure, software and algorithms may be used intechangeably.

In one preferred embodiment, the signals from the probe are brought into a computer based system. The computer based system may be a cardiac mapping system, a cardiac monitoring/recording system, or a stand alone system.

Figure 8A:
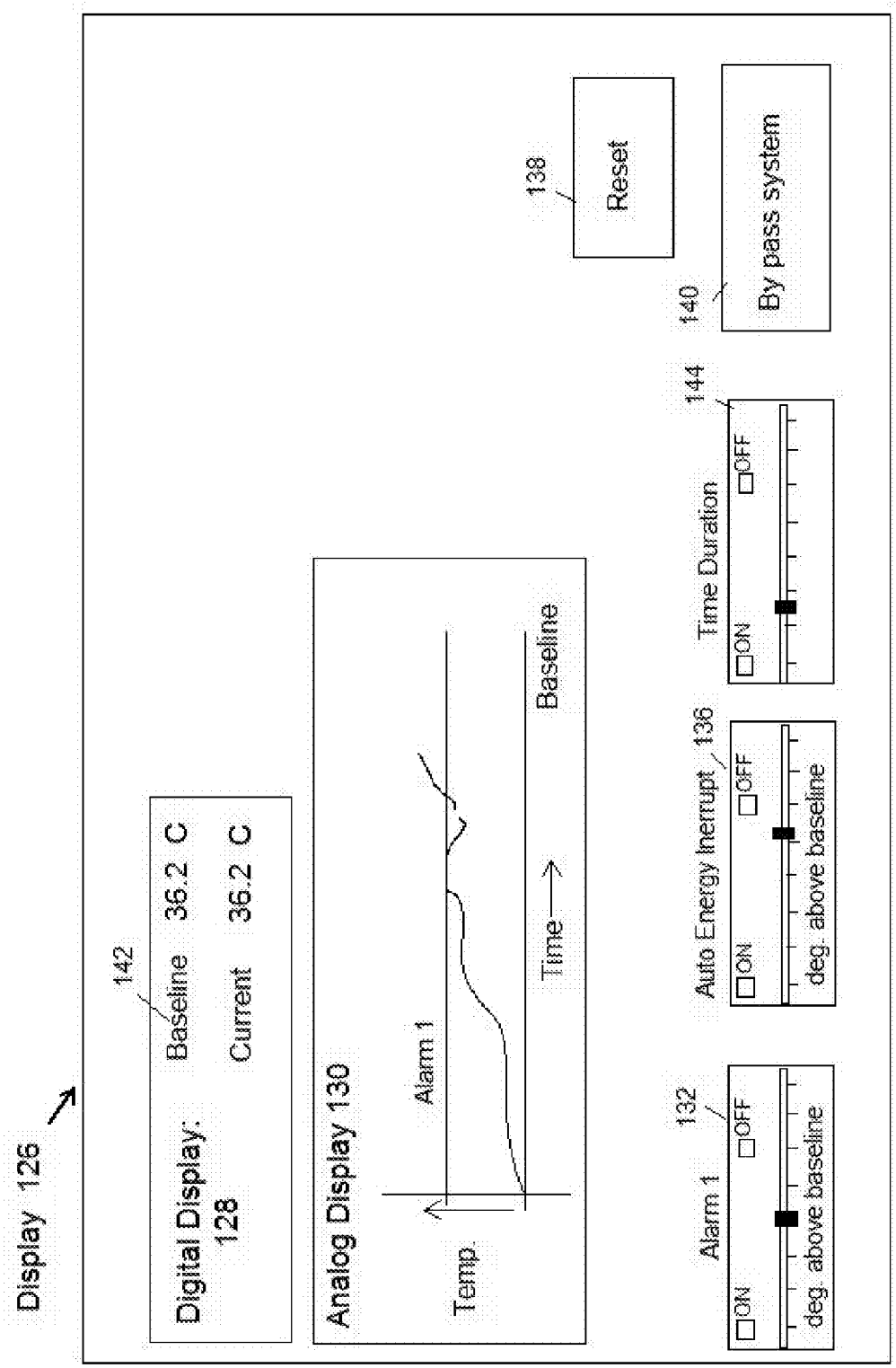
FIG. 8A shows an example of graphical display and graphical interface of the concept.

The slaved signals 88 which are brought into the separate computer 103 (via the interface box 89) are analyzed and displayed 101. The display is both in the form of graphs and digital readout of temperature, and is described later in conjunction with FIGS. 8A, 8B, 9D. The computer 103 comprises software which is configured and programmed to monitor temperature levels, and trigger one or more level(s) of alarm(s) and/or activate ablation interrupt, when predetermined threshold limits are reached. In one aspect, at the start of the ablation procedure the baseline temperature of the patient is set into the computer by the operator. This value acts as the baseline for any increase in temperature as the ablation procedure progresses, and various lesions are delivered. Typically numerous lesions are delivered during the course of the ablation procedure. Without limitation in one embodiment, there are two levels of alarms, after which an automatic interrupt takes over computer controlled by a relay switch or other interrupt means. In another embodiment, there are more than two levels of alarms.

The following description is meant to be illustrative and not limiting. In one embodiment the first alarm is set to a first value, which is a threshold value that can be easily entered or adjusted on the graphical interface of the computer (shown later in conjunction with FIG. 8A, 8B, 9D). When the first level of alarm is reached there is both sound warning and an optional light warning coming from the interface box (or the computer). When the second level of alarm is reached, both the audio and visual levels get stronger (or more intense). Finally, when the temperature reaches the next level, which is pre-determined or pre-defined by the healthcare operator, there is a computer controlled temporary interrupt or shut-off of the energy delivery from the ablation generator 104. As shown in conjunction with FIG. 2A, upon detection of the limit by the software the computer 103 gives a command signal via the interface box 89, such that the relay switch 108 (as one example of interrupt means) which is placed in the ablation circuit is opened and the energy delivery is interrupted. At this point, the physician either repositions the catheter to a site further away from the esophagus 110, or waits for the temperature to come back down. The ablation energy delivery can be re-started at any time by simply re-setting the switch using either a software or a hardware switch.

In the example of the above embodiment, say the physician has the first alarm set to a level of 0.25° C., the second alarm set to a level of 0.50° C., and the third alarm set to a level of 1.0° C. When the temperature increases to above 0.25° C. of the baseline, a beep or buzzer sound is activated along with the flashing light. At this point the physician may steer the catheter to a site which is further away from the esophagus 110 or may hold off on the energy delivery, or may finish the current burn being aware that this is the first alarm. If the temperature continues going up, and reaches the pre-determined threshold for the second level of alarm, the physician may more readily interrupt the ablation burn, unless at a critical point or seconds away from finishing the current burn. If at any time, the temperature reaches the threshold for automatic interrupt or shut-off, a command signal from the computer 103 via the output side of the interface box 89, opens the relay switch 108 interrupting the ablation circuit, and stopping the energy delivery to the tissues. At this point the physician or the operator resets the circuit. Again the physician may keep ablating after moving the catheter to a site which is further away from the esophagus 110 or wait until the temperature drops back down to a normal level before ablating again.

An example of first alarm may be a buzzer, a tone, or intermittent beeps. In such a case the second alarm may be a higher level of buzzer, tone, or more frequent beeps indicating a higher level of concern than the first alarm. In the case of a flashing light or LED, the second level of alarm may be more rapid and more intense flashing or higher frequency of LED flashing. There may also be an additional voice message also reciting the values of the temperature measurement. The above are examples only, and are not meant to be limiting. In the case of an automatic computer based interrupt or shut-off, the software may be configured and programmed such that as the temperature drops back to a pre-determined normal level, the system switch will reset itself.

Since sustained elevated temperatures may be related to thermal injury, in one embodiment the automated shut-off may be a combination of higher than baseline temperature and time duration. For example the elevated temperatures stay at a higher level for an adjustable and programmable period of time. Therefore in this embodiment the auto shut-off is based on increases in temperature and time duration of elevated temperature.

Figure 2B:
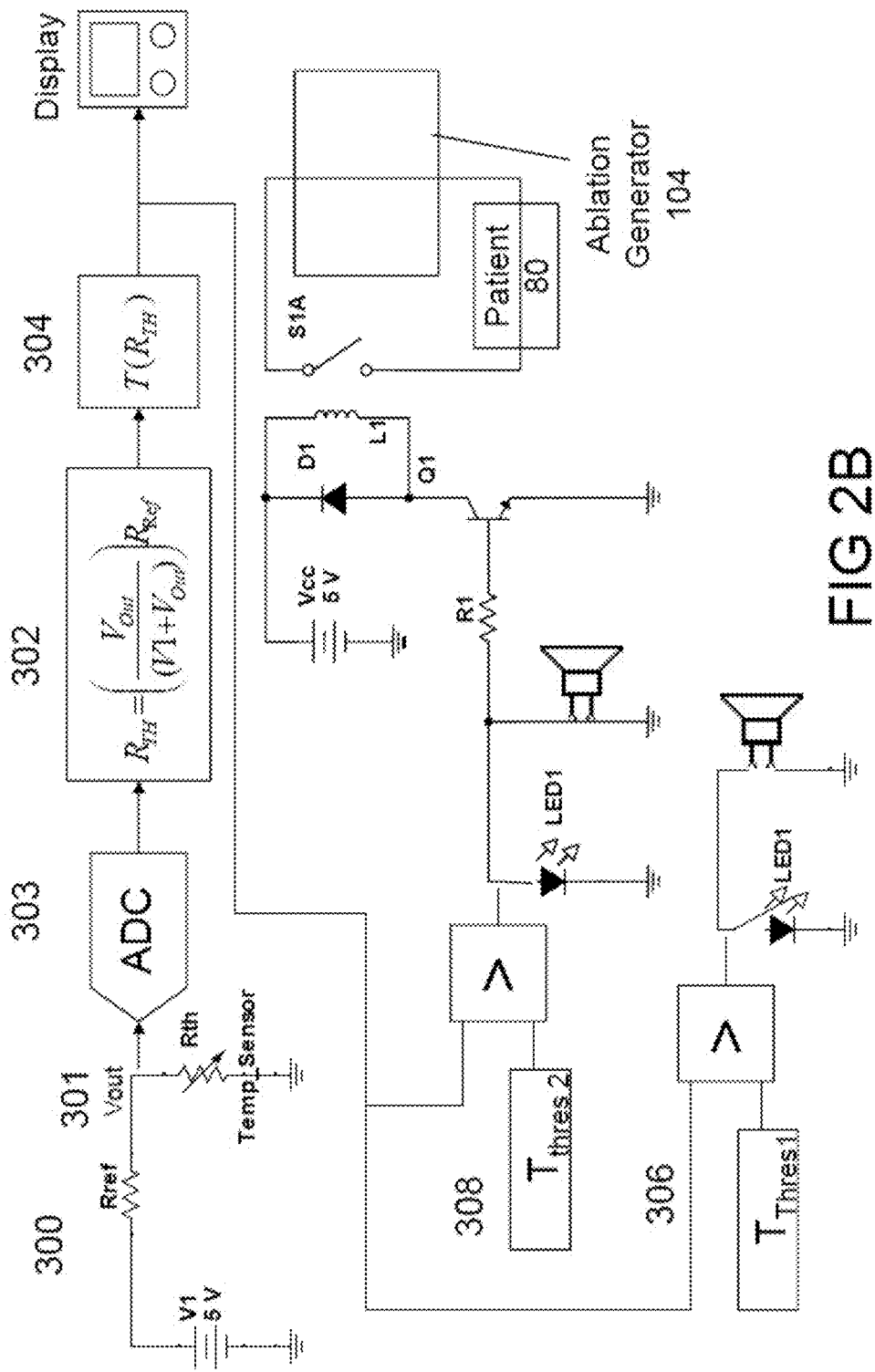
FIG. 2B depicts one implementation of the system and method.

Shown in FIG. 2B is a block and circuit diagram for one implementation of this disclosure. Other functionally equivalent circuitry can also be used. The temperature sensor setup in block 300 outputs a voltage that varies with temperature 301, in a thermister based system. The analog voltage signal is converted to digital signal by the ADC 303 and transformed to an impedance change 302 where $R_{Ref}$ is a reference resistor chosen close to operating impedance of the temperature sensor. Shown in block 304, the impedance is converted to a temperature change using sensor specifications.

The temperature is compared to the first threshold 306 and if it's greater, an LED 307 and sound alarm 309 are activated. As shown in 308, if the temperature exceeds the second threshold, a relay is also activated that switches off the ablation generator 104 or interrupts the energy delivery. Using similar methodology, more than one level of alarm may be used (not shown in the figure).

It will be clear to one of ordinary skill in the art, that the above concept can be practiced in various ways. For example, as shown in conjunction with FIG. 3, instead of splitting or slaving the temperature signal into both the patient monitor and another computer 103, the second set of signals to computer 103 may be gotten directly from the patient monitoring system 86 into the interface box. This simplifies the connections, providing that there is an output available from the patient monitoring system 86.

In one embodiment, the concept may be practiced independent of the patient monitoring system or anesthesia monitoring system. In this embodiment, as shown in conjunction with FIG. 4, the esophageal temperature probe 112 is connected directly to the interface box 89, which sends signals to the computer 103 which has the processor 100 with software configured and programmed with algorithms 102 capable of detecting pre-determined events. In this embodiment the anesthesiologist is relieved of the burden of monitoring esophageal temperature.

In one embodiment, the algorithms for detection of esophageal temperature alarm 102, limits and logic for automatic computer shut-off or interrupt 106 may be incorporated into the computer of a patient monitoring system 86. This embodiment is shown schematically in conjunction with FIG. 5. The esophageal probe 112 is connected to the monitoring system or anesthesia monitoring system 86 in the usual manner. In this embodiment, the software with algorithms 102 of the system 116 is configured and programmed to incorporate the algorithms for detection of out of range limits. Further, under conditions where an automatic interrupt or shut-off is warranted, an interface unit 117 connects to the relay switch 108 (or other interrupt means) for the shut-off or interrupt. In this embodiment, the patient monitoring system 116 is also configured with audio alarms, visual alarms, and voice messages 105. The advantage of this embodiment is that a second parallel computer is not required.

Figure 6:
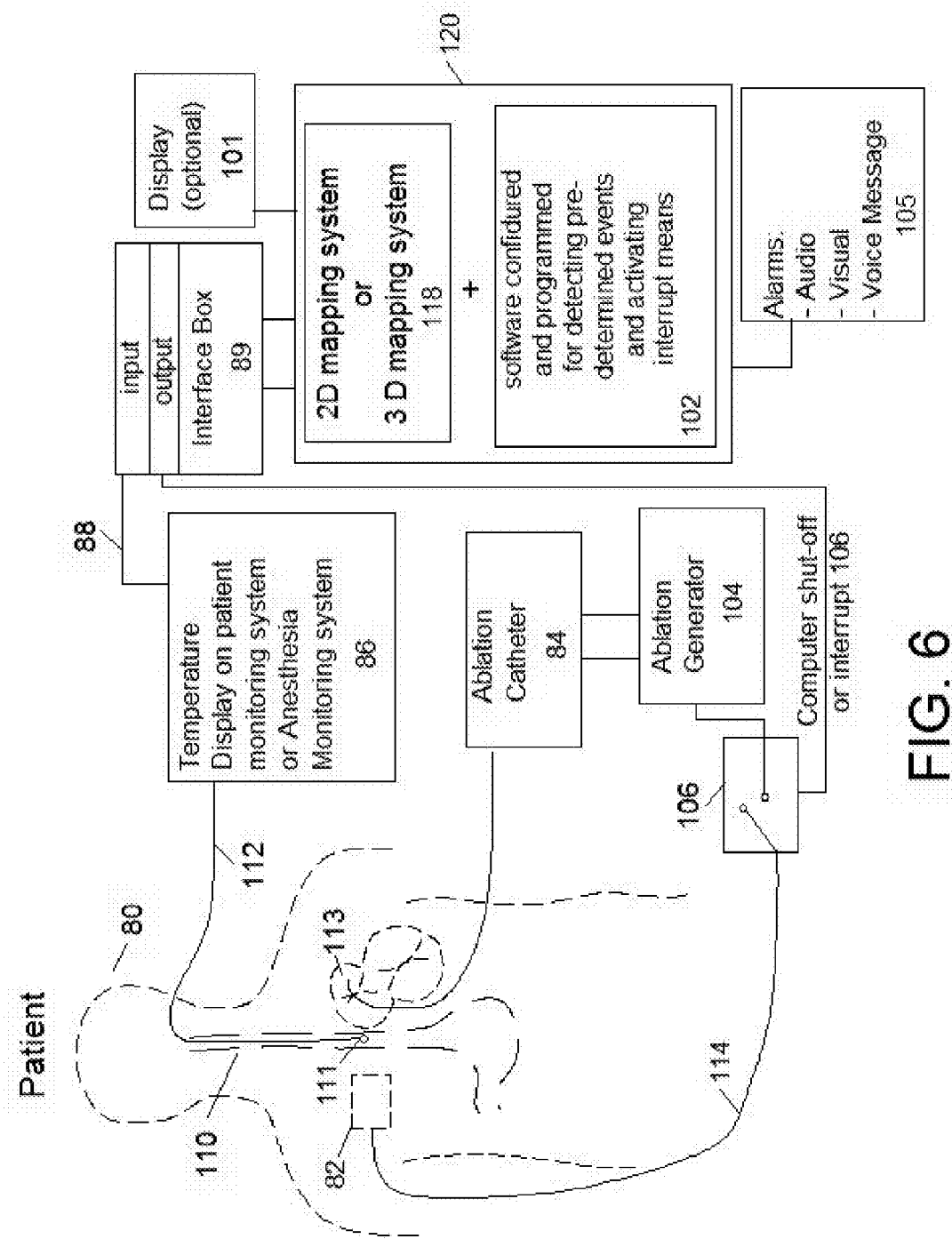
FIG. 6 depicts a general setup of the concept where the esophageal signals from the patient are split and slaved into a 2-D or 3-D mapping system, and where the logic for alarms and automatic interrupt is incorporated within the 2-D or 3-D mapping system.

In another embodiment, the software algorithms for esophageal temperature monitoring and out-of-range limit alarms may be incorporated into a 2-D cardiac electrophysiology recording or monitoring system, or a 3-D cardiac mapping system. This is shown in conjunction with FIG. 6. Examples of 2-D cardiac electrophysiology systems include, the CardioLab™ system of GE Healthcare, CR Bard's recording system, and electrophysiology recording system marketed by St. Jude Medical. Examples of 3-D mapping systems include Biosense Webster's Carto™ mapping system, St Jude's Navix™ mapping system, and a mapping system by Boston Scientific's Rhythmia Medical's mapping system. In this embodiment, as shown in conjunction with FIG. 6, the esophageal probe 112 signal is either slaved 88 into the electrophysiology monitoring or recording system 118 via an interface box 89 or directly connected to cardiac recording or mapping system (not shown). In this embodiment, the software of the monitoring system or mapping system 120 is configured and programmed such that the algorithms for detection of out of range limits for esophageal temperature are incorporated. As shown in FIG. 6, the system 120 also controls the automatic shut-off or interrupt and the audio, visual and voice messages 105.

Figure 7:
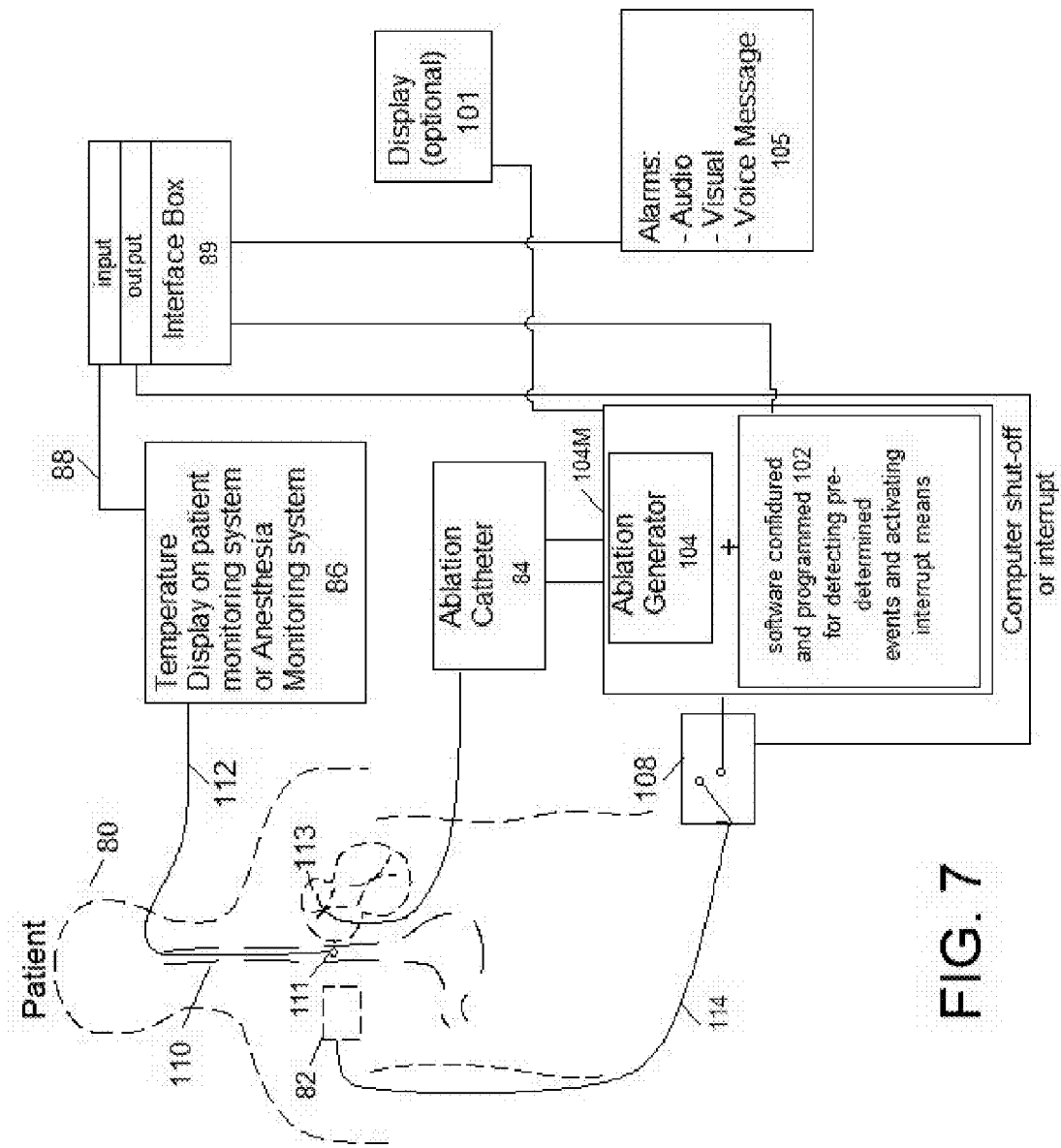
FIG. 7 depicts a general setup of the concept where the esophageal signals from the patient are split and slaved into the ablation generator, and the logic for alarms and automatic interrupt is incorporated into the ablation generator system.

In another embodiment, the algorithms for temperature monitoring and out of range limit alarms may be incorporated in the ablation generator system 104M. This is shown in conjunction with FIG. 7. In this embodiment, the standard ablation generator 104 is modified such that the controller in the modified ablation generator 104M comprises software which is configured and programmed to handle the algorithms for temperature monitoring from the esophagus 110, and implement out of range limit alarms 105 and computer shut-off or interrupt 106. As shown in FIG. 7, in this embodiment, the temperature probe signals are slaved and are connected to the modified ablation generator 104M via an interface box 89. The logic functions of alarms 105 and interrupt 106 are now configured and programmed 102 within the ablation generator 104M.

Figure 3:
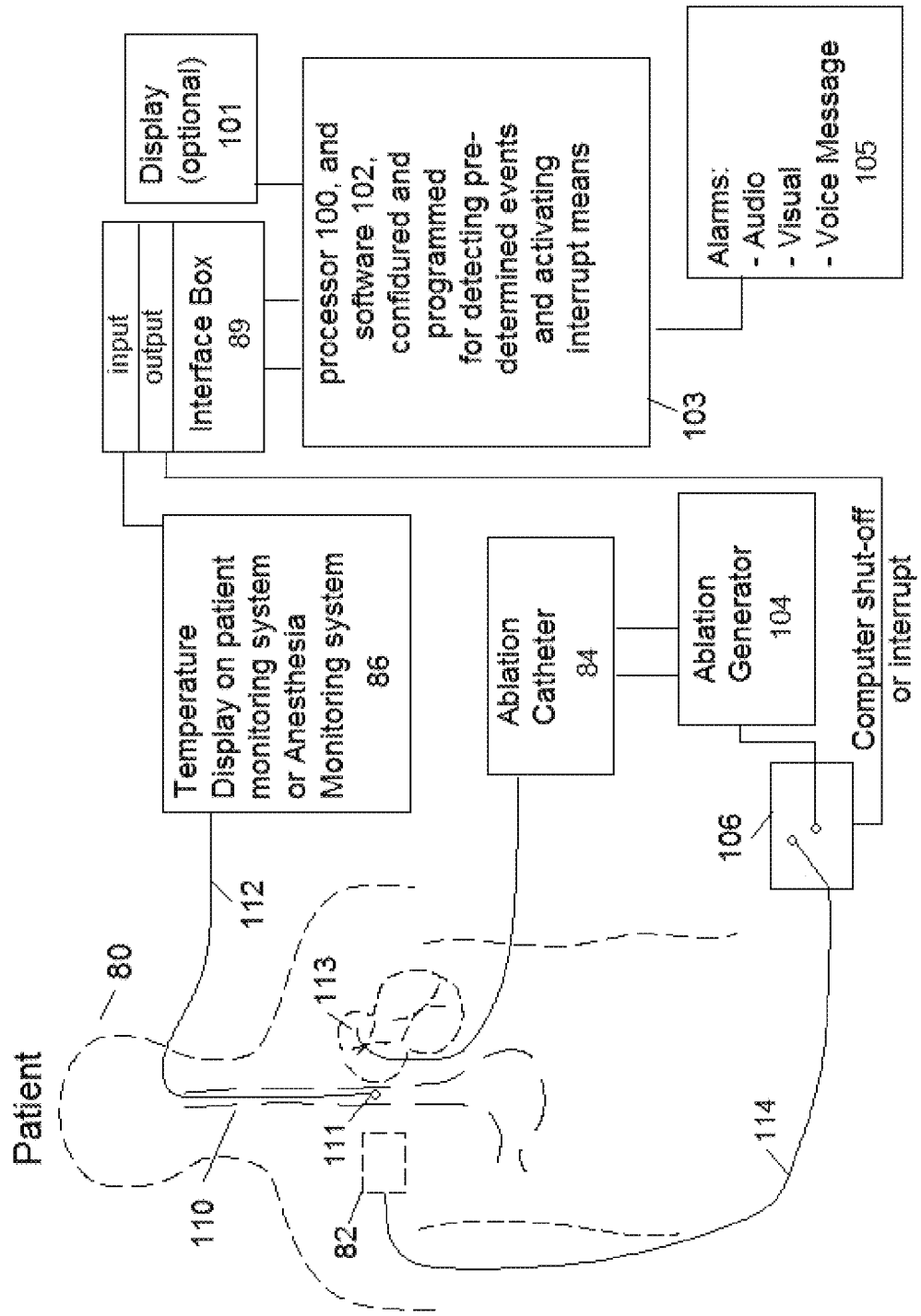
FIG. 3 depicts a general setup of the concept where the esophageal signals from the patient are brought into another computer from the patient monitoring system.
Figure 4:
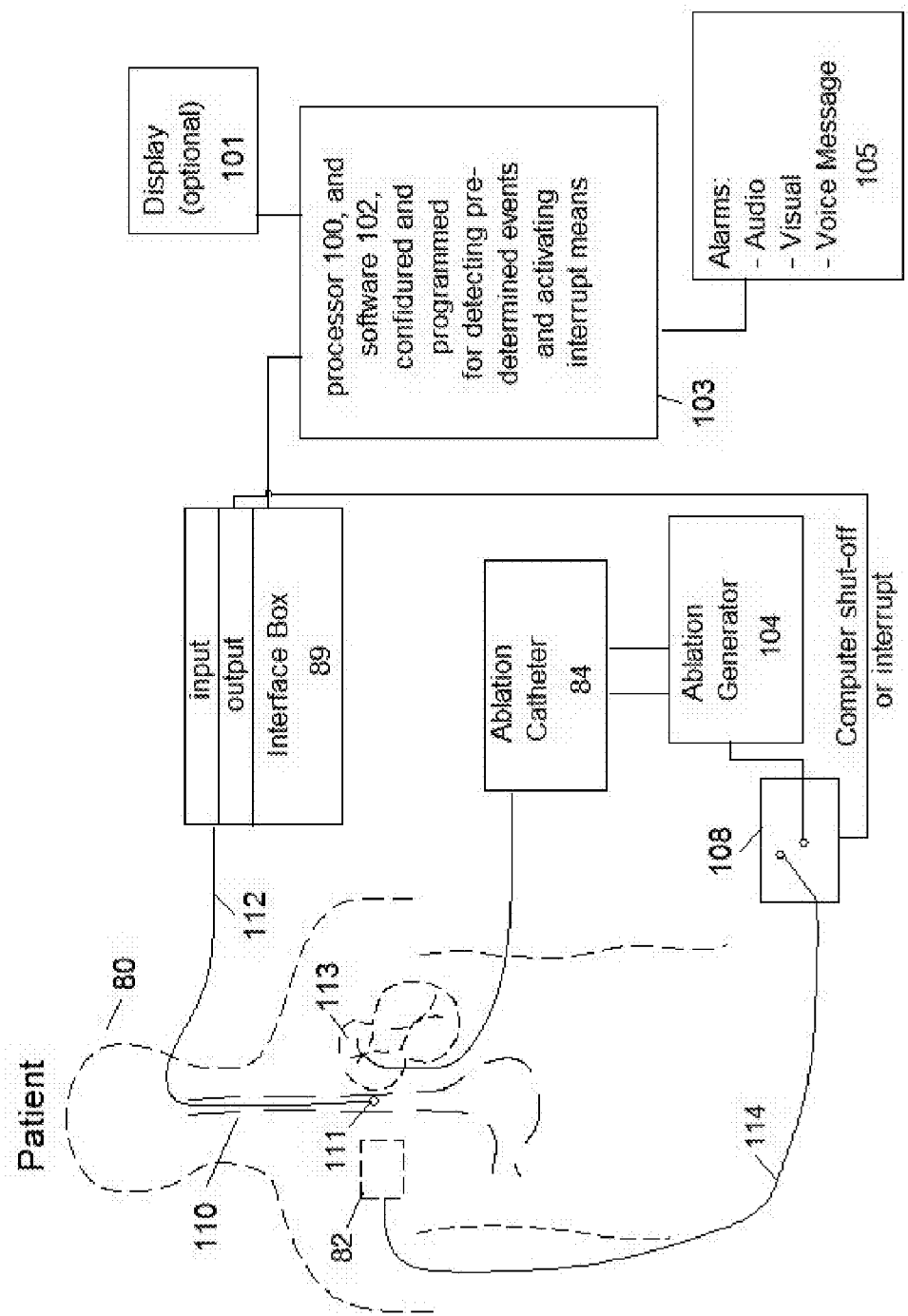
FIG. 4 depicts a general setup of the concept where the esophageal signals are brought into a computer for monitoring without using the patient monitoring system.
Figure 5:
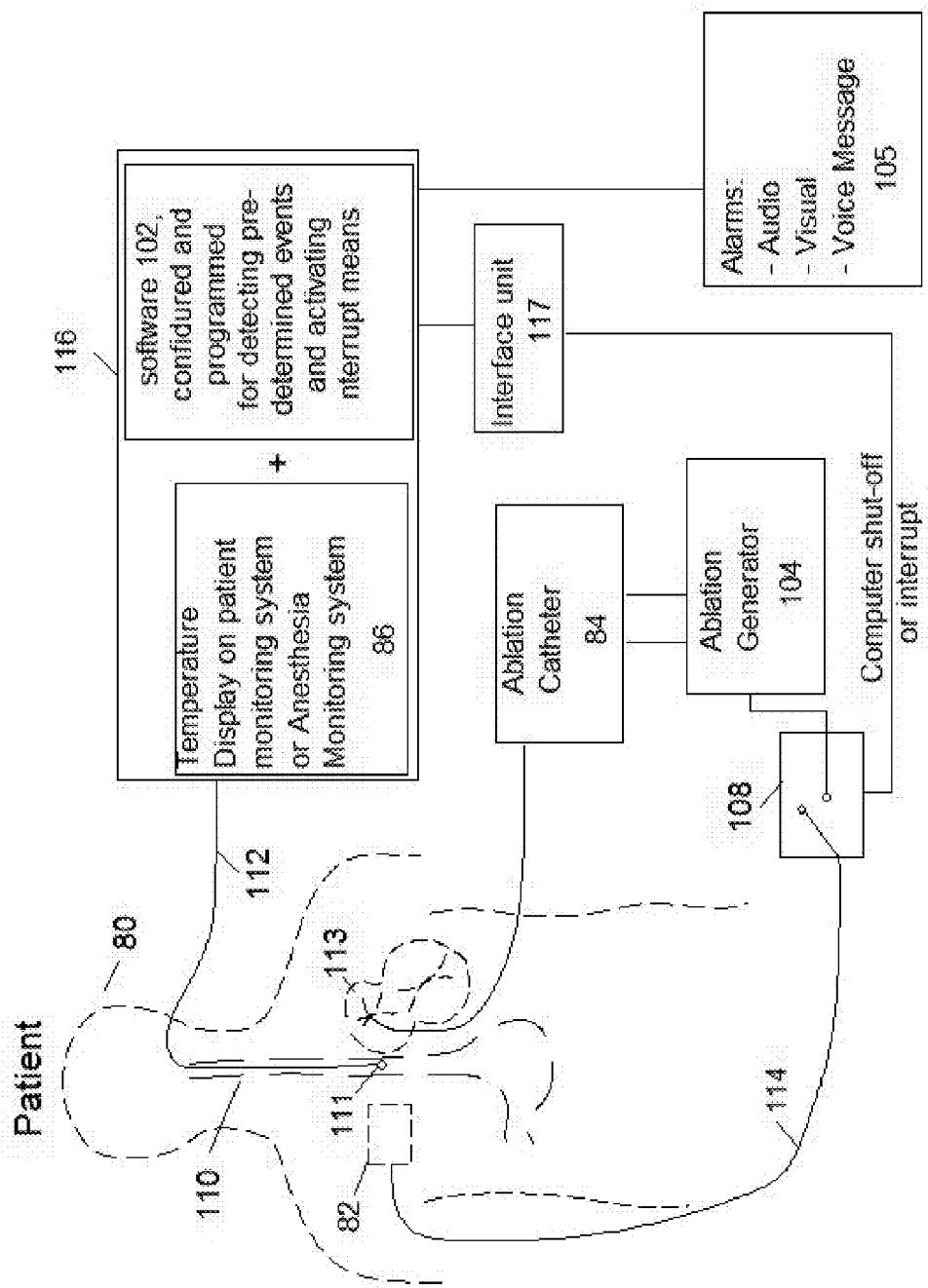
FIG. 5 depicts a general setup of the concept where the esophageal signals are monitored by the patient monitoring system and the logic for alarms and automatic interrupt is incorporated into the patient monitoring system.

As was shown in FIG. 3, the computer 103 has a display 101. This is shown in conjunction with FIGS. 8A & 8B as display 126. There is both a digital display 128, and an analog display 130. At the beginning of the atrial fibrillation ablation procedure the baseline temperature 142 is updated. Following that, the computer program tracks the temperature relative to the baseline 142. First alarm (Alarm 1) 132 can be turned ON or OFF. In one example, there is a simple sliding scale to program the threshold level for the first alarm provided it is turned ON. Similarly, a second alarm (Alarm 2) 134 (shown in FIG. 8B) can be turned ON or OFF. If Alarm 2 is turned ON, the threshold level for Alarm 2 is greater than Alarm 1, and can be adjusted simply by the sliding scale in this example.

In addition to the first and second alarms, there is an Auto shut-off feature 136 also. The Auto shut-off 136 feature may be used in conjunction with Alarm 1 and Alarm 2, or the two alarms may be turned OFF and Auto shut-off 136 may used alone by itself. The threshold criteria for the Auto shut-off 136 can be entered in a similar manner by adjusting the sliding scale. There is a Reset button 138 for bringing all the values to default values, and adjusting the parameters again. As shown in the figure, there is a Bypass button 140, to take the computer and system out of the loop from the ablation procedure, if an operator so desires for any reason.

FIG. 8B shows an example of graphical display and graphical interface of the concept with two levels of alarms, alarm 1 and alarm 2.

It will be clear to one skilled in the art that various different softwares may be used in implementing this concept and methodology. Program code can be written using one of several commercially available software packages. The software that can be used for this purpose is LAB WINDOWS/CVI, LABVIEW (National Instruments Corp.), C+, Microsoft Visual C++, Dot Net framework, MATLAB, and Microsoft Visual Basic, among others. Use of these or other comparable languages for this purpose that are available now or developed in the future, is considered within the scope of the disclosure. Testing of applicant's prototype has been performed using Microsoft visual C++, LabView and MATLAB.

FIG. 9A summarizes schematically the ablation circuit and its relation to esophageal temperature monitoring circuit and automatic interrupt of ablation energy delivery. Signal from the esophageal probe 112 is brought into the computer 103 via the interface box 89. Computer 103 comprises software configured and programmed with algorithms 102 capable of detecting pre-determined events and computer based interrupt of energy delivery. When a pre-determined threshold criteria is met, the control switch will interrupt the ablation energy delivery to the circuit. As shown in the figure, energy interrupt means 106 is placed in the return path of the ablation circuit. Alternatively, the energy interrupt means 106 can also be placed on the catheter side of the circuit.

In one aspect of the disclosure, instead of just indicating alarms and interrupting energy delivery, active attempt is made to cool the esophagus. In one aspect active cooling of the esophagus is performed by itself. In another aspect of the disclosure active cooling of the esophagus is performed in conjunction with various alarm(s) and automatic interrupt.

Figure 9B:
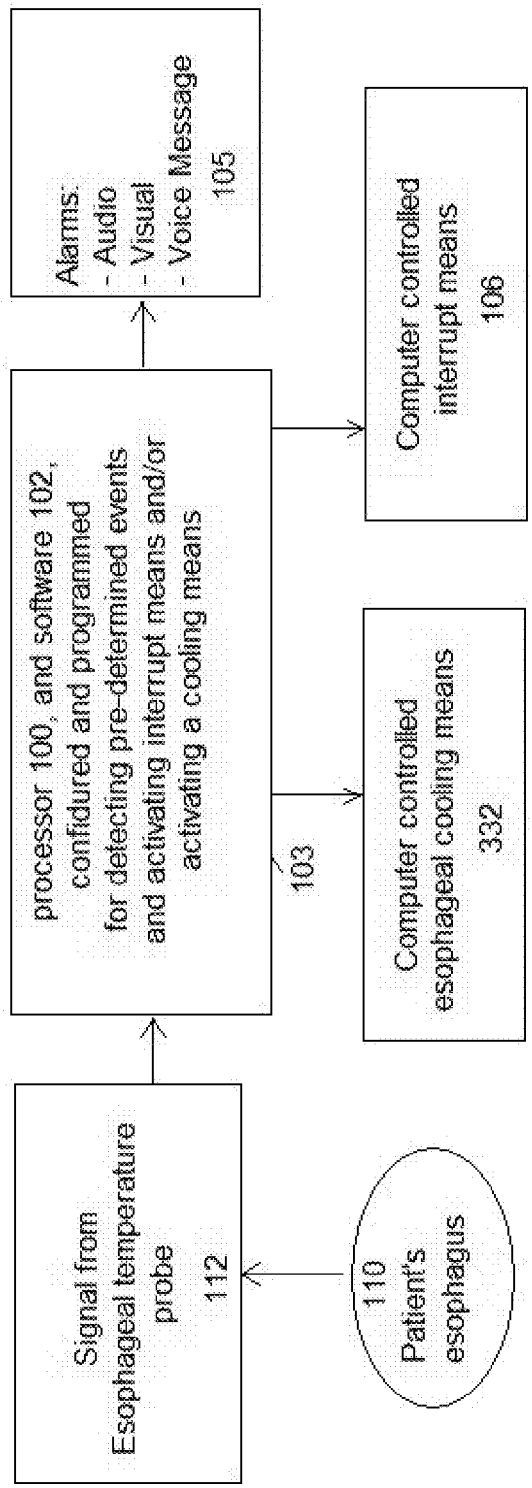
FIG. 9B depicts in block diagram the concept with computer controlled esophageal cooling means.
Figure 9D:
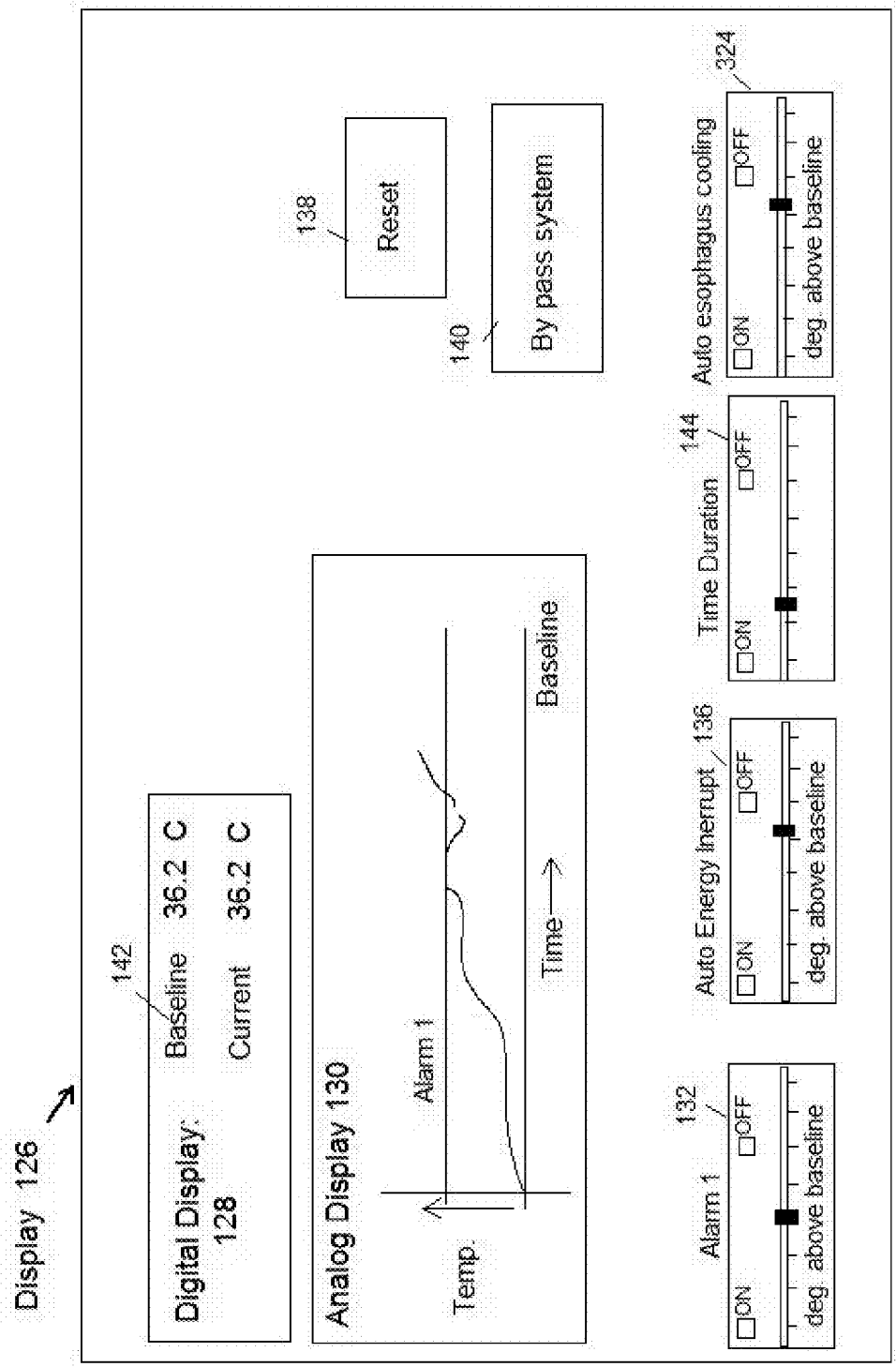
FIG. 9D shows an example of graphical display and graphical interface of the concept with Auto esophagus cooling.

Shown in conjunction with FIG. 9B, as before a temperature probe 112 is inserted into the esophagus 110. Additionally, apparatus for cooling the esophagus is also inserted. In one aspect it is a saline balloon which is flushed with cool saline from an external saline bag. For the practice of this disclosure any other means of cooling the esophagus 100 may be used. As shown in FIG. 9B the esophageal cooling apparatus is controlled by a controller based on pre-programmed algorithms.

Saline or salt water typically freezes at 39° F. Therefore, without limitation in one embodiment temperatures in the range of approximately 40° F. and 55° F. may be used. Other temperatures may also be used. The decision of the temperatures will generally be determined by the lab.

Shown in FIG. 9C is one embodiment of this invention. As shown in the figure, in this embodiment a modified esophageal temperature probe 318 includes a balloon 310 which can be filled with cold saline to cool the temperature of the esophagus 110. The cold saline is supplied from a saline bag 314 which may be placed on a stand similar to a saline drip, which is common in procedure rooms. As also shown in the figure, the flow of cold saline is controlled by controller 103, which receives its input from the temperature probe based on the programmed values. It may also be controlled by a separate controller. Therefore in one embodiment as the esophageal temperature reaches a pre-determined level, an alarm may be activated. Additionally, as the esophageal temperature reaches the next pre-determined level, cool saline may be deposited in a balloon or pouch 310 which is located adjacent to the temperature probe 111 inside the esophagus. Further, if the temperature increases further to a next pre-determined level, the ablation energy may be interrupted. All of the above events will be activated according to the program setting as entered by the operator. FIG. 9E shows the display for this embodiment.

It will be clear to one skilled in the art that pre-determined event(s) can trigger alarm(s), an energy interrupt, or esophageal cooling means or any combination of these.

Figure 10:
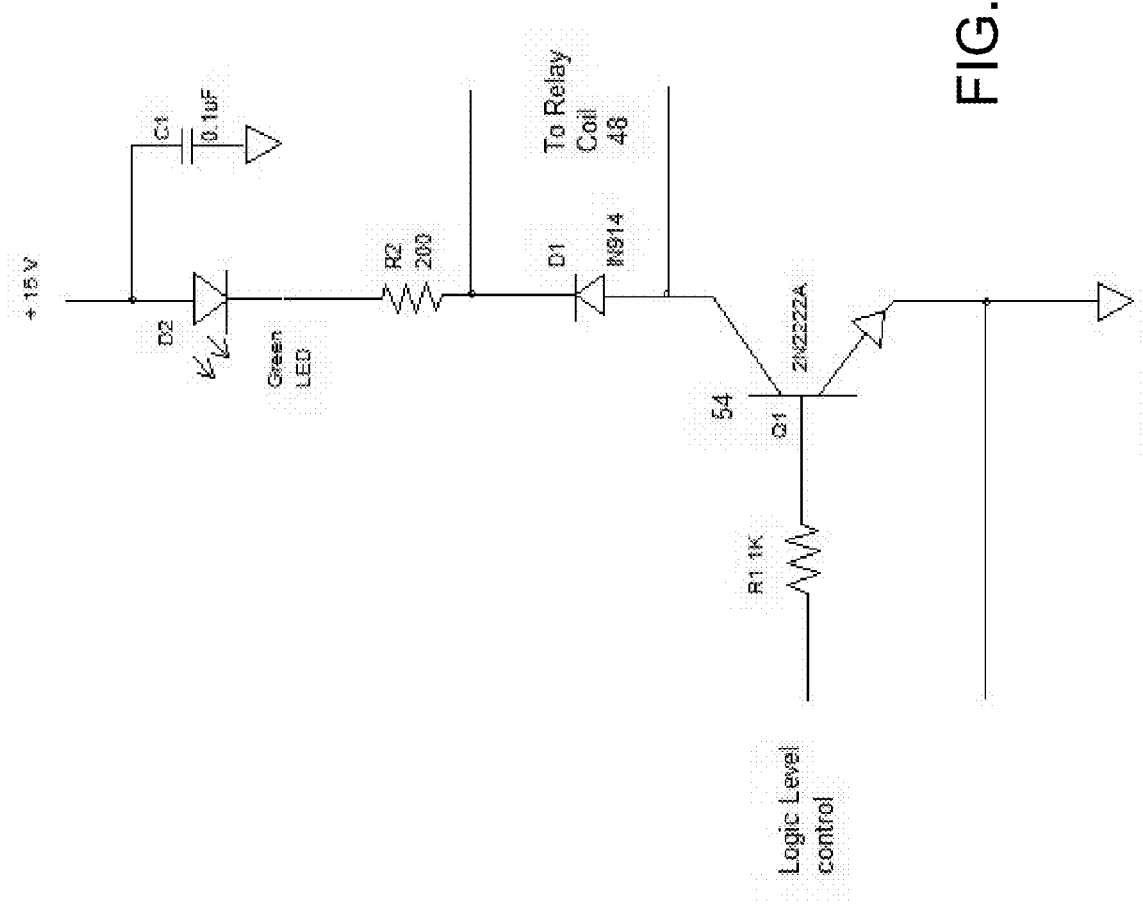
FIG. 10 is an electrical schematic for the control of the relay switch.
Figure 11:
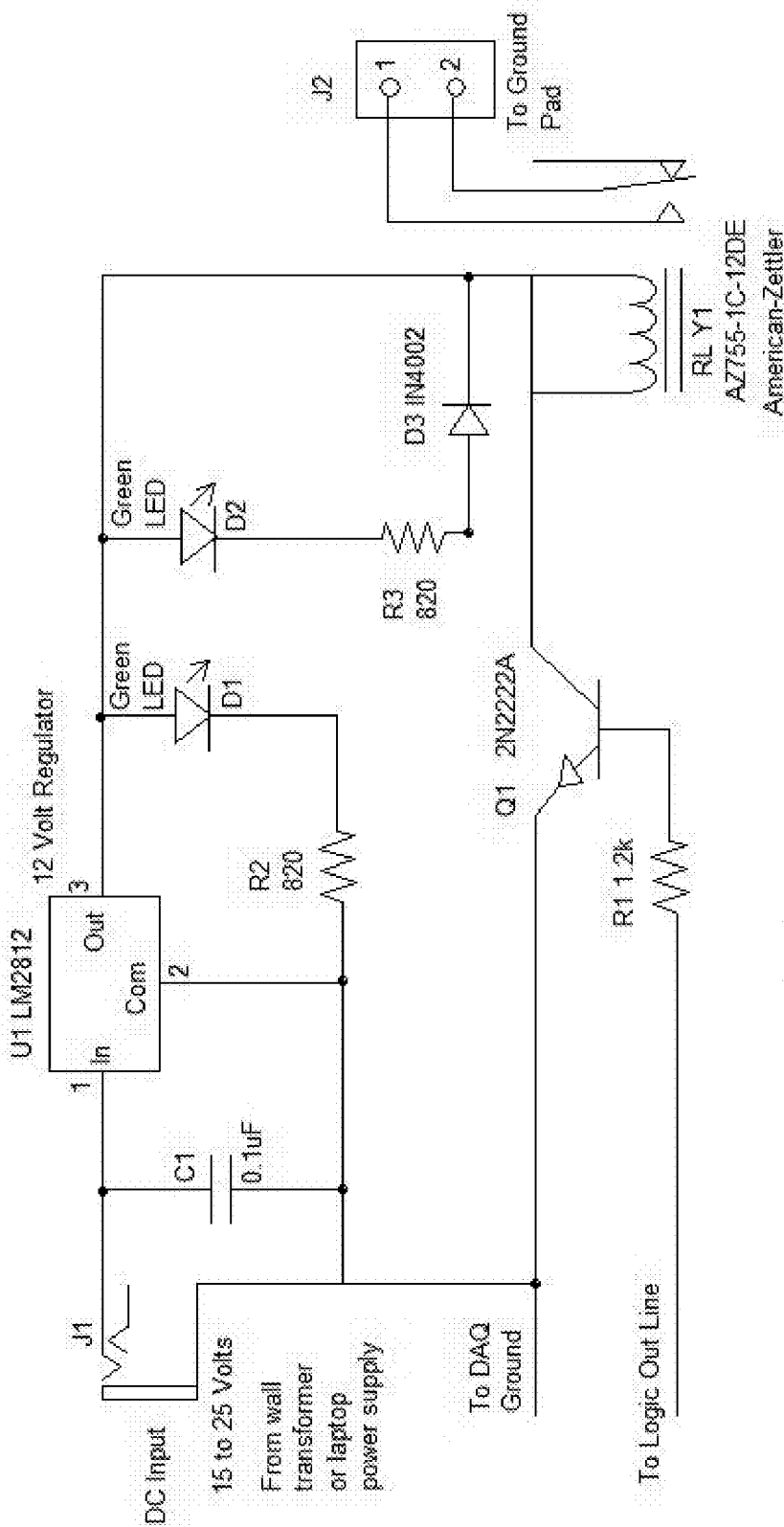
FIG. 11 shows one example of the relay switch.

The circuitry for one example of the control switch is shown in conjunction with FIGS. 10 and 11. FIG. 10 shows a simplified circuit to drive a relay coil 48, which interrupts the ground loop side of the ablation circuit. As shown in the figure, when the logic level control 54 goes high, there is current flow at the base of transistor Q1 (54), and transistor Q1 conducts, energizing the Relay coil 48. The logic level control 54 is high only when certain pre-determined conditions are met. The pre-determined conditions are derived by analysis of signals and are based on safety conditions for esophageal temperature change.

Most ablation generators on the market have maximum impedance cut-off and delta impedance cut-off features. In this feature, when the impedance increases over the adjusted maximum cut-off value or is infinite (e.g. if the connection to the catheter is broken) the ablation generator will switch off automatically and an error message "Imped. too high" will be displayed in one example.

Using this feature of the ablation generator, shown in FIG. 11 is one implementation for practicing this method. In this embodiment, Logic High energizes the relay, thereby shutting off the ablation generator.

As shown in conjunction with FIG. 11, a relay switch circuitry is connected in the ground patch electrode 23. In this configuration, a transistor Q1 54 performs the switching. When the Logic Out Line from the DAQ goes "high", the relay is energized. Power to the circuit may be supplied by a wall transformer or laptop power supply. The logic out line from DAQ is controlled by the software.

Figure 12:
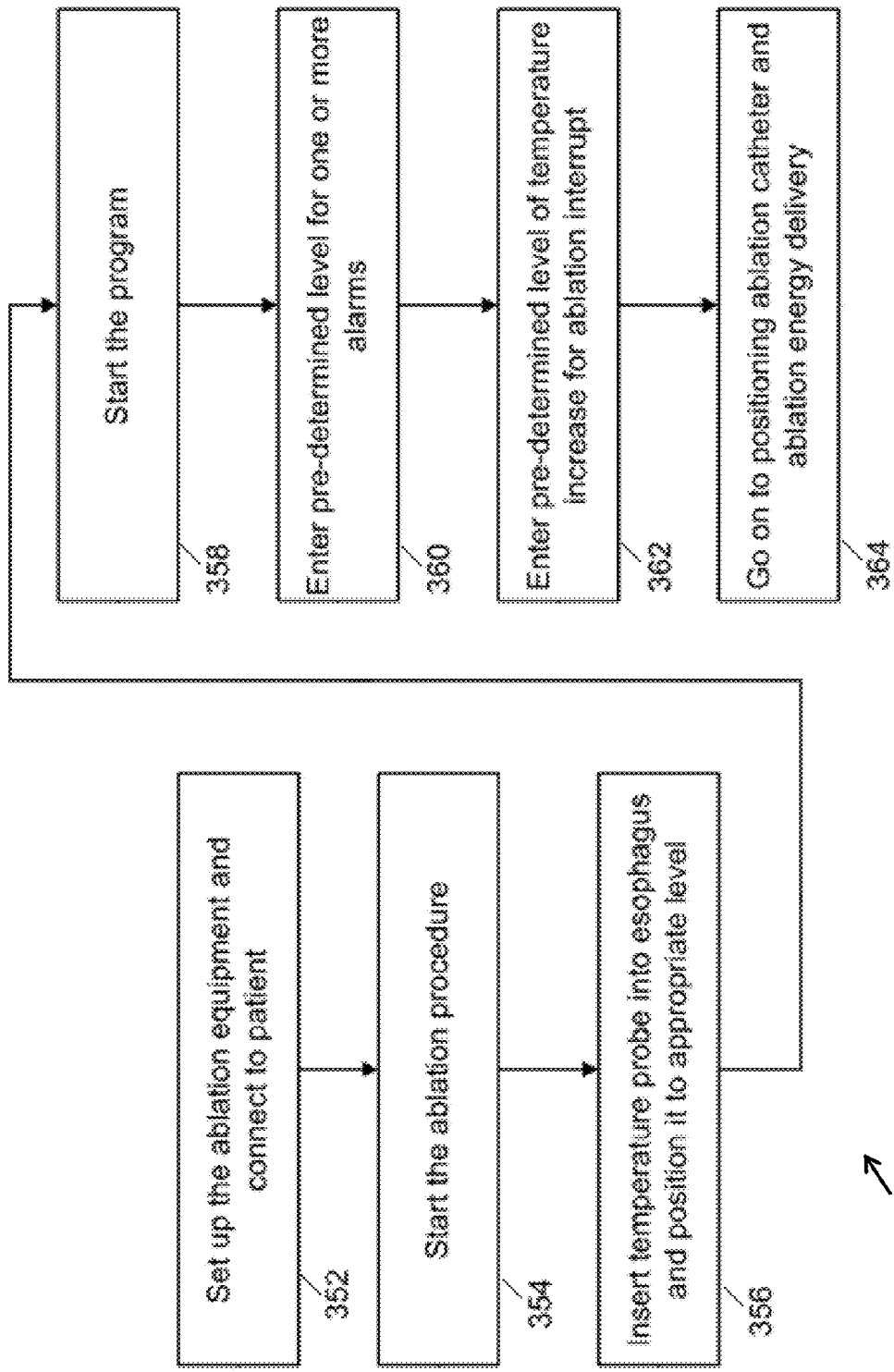
FIG. 12 is an overall flow diagram of the method of the concept

FIG. 12 depicts a flowchart of a typical procedure. The flowchart 350 begins at block 352 where the equipment is set up and connected to the patient. The procedure begins as shown in block 354. The temperature probe is positioned in the esophagus, block 356 and the program is started block 360. The operator enters pre-determined levels for one or more alarms 360 as determined by the physician. The operator also enters per-determined level of temperature increase for ablation interrupt 362, also as determined by the physician. The ablation catheter is then positioned and ablation energy is started as shown in step 364.

In one aspect, a temperature probe comprising multiple thermisters is utilized. Any number of thermistors on an esophageal probe may be utilized. An advantage of multiple thermistors is that it covers a relatively larger area of the esophagus, as opposed to a small segment with just one thermistor. Advantageously, the temperature probe with multiple thermistors does not have to be moved, or re-positioned less often once it is initially placed in the esophagus. Further, it will even protect patients with large left atrial sizes. The overall concept utilizing esophageal probe with multiple thermistor (or thermocouples) is shown in conjunction with FIG. 13. In this disclosure, even though examples are shown with 10 and 12 thermistor probes (sensors) on the esophageal probe, it will be clear to one skilled in the art, that with slight modification of the hardware and software, any number of thermistors (or thermocouples) may be utilized.

Figure 13:
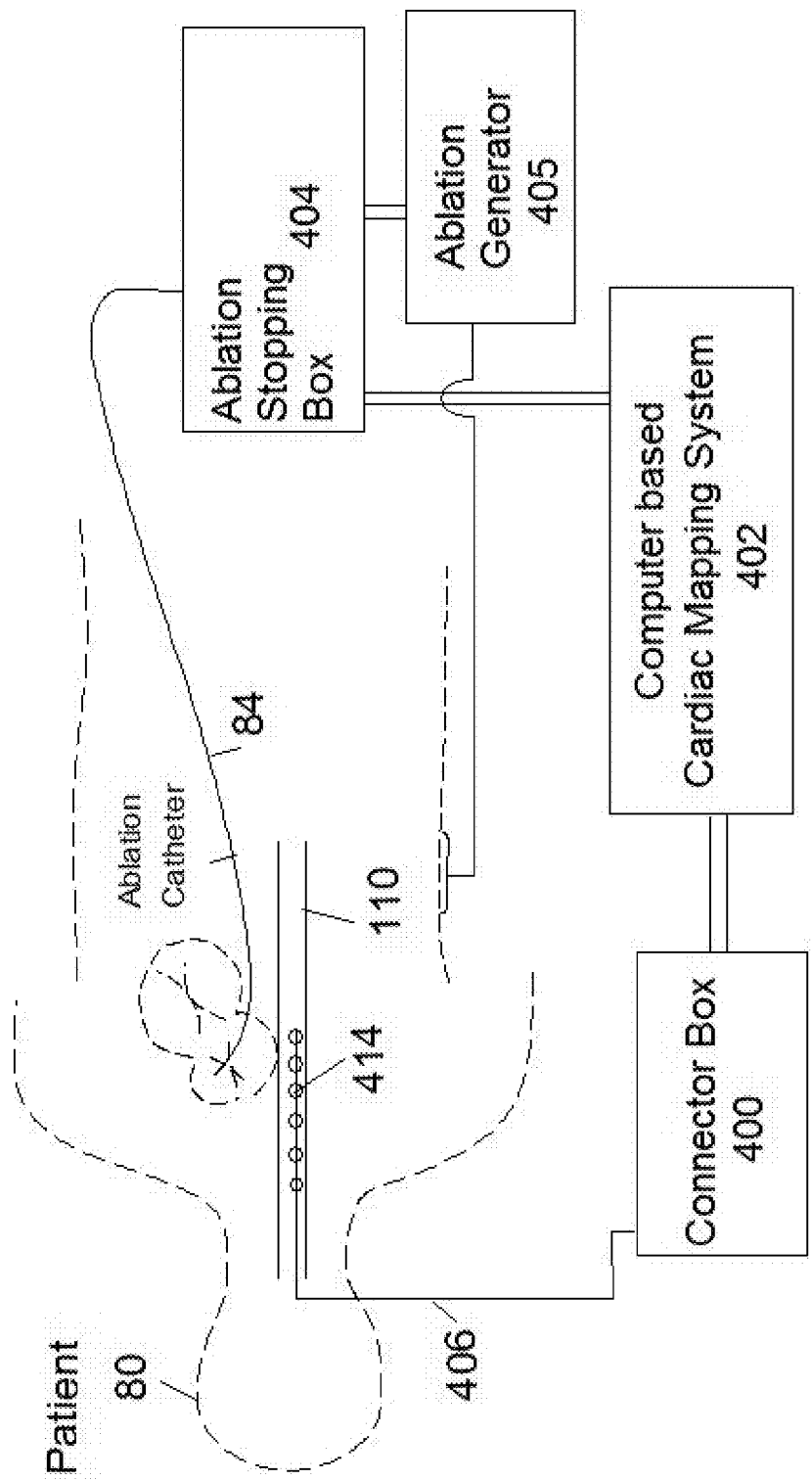
FIG. 13 is a block diagram of overall concept showing monitoring of temperature from an esophageal probe and processing temperature information in a cardiac mapping system.
Figure 14:
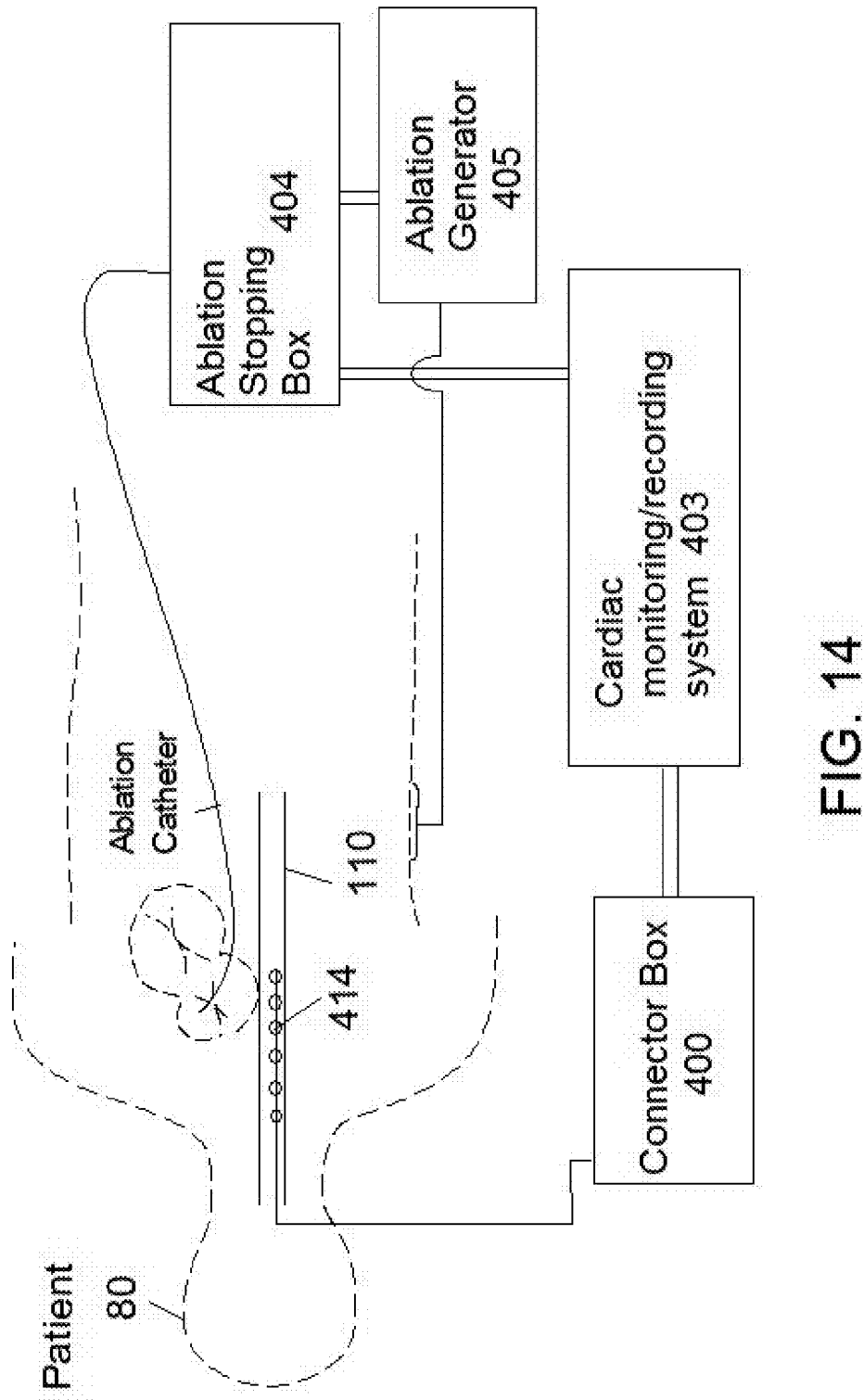
FIG. 14 is a block diagram of overall concept showing monitoring of temperature from an esophageal probe and processing temperature information in a cardiac monitor/recording system.

As shown in FIG. 13, patient 80 is inserted with a multiple thermistor esophageal probe 414. The temperature information from the esophageal probe 414 is brought into a cardiac mapping system 402 (or cardiac monitoring/recording system 403, shown in FIG. 14) via an interface connector box 400.

The cardiac mapping system 402, may also be connected to an ablation stopping box 404 (or energy interrupt box 404). The ablation interrupt box 404 is connected in-between the ablation catheter 84 and the ablation generator 405. Based on a command signal from the cardiac mapping system 402, the ablation stopping box 404, which is between the ablation catheter 84 and the ablation generator 405, interrupts the energy delivery of the ablation catheter 84 during the procedure, based on reaching the criteria of pre-determined conditions set by the operator or the physician, before the ablation starts.

Figure 15:
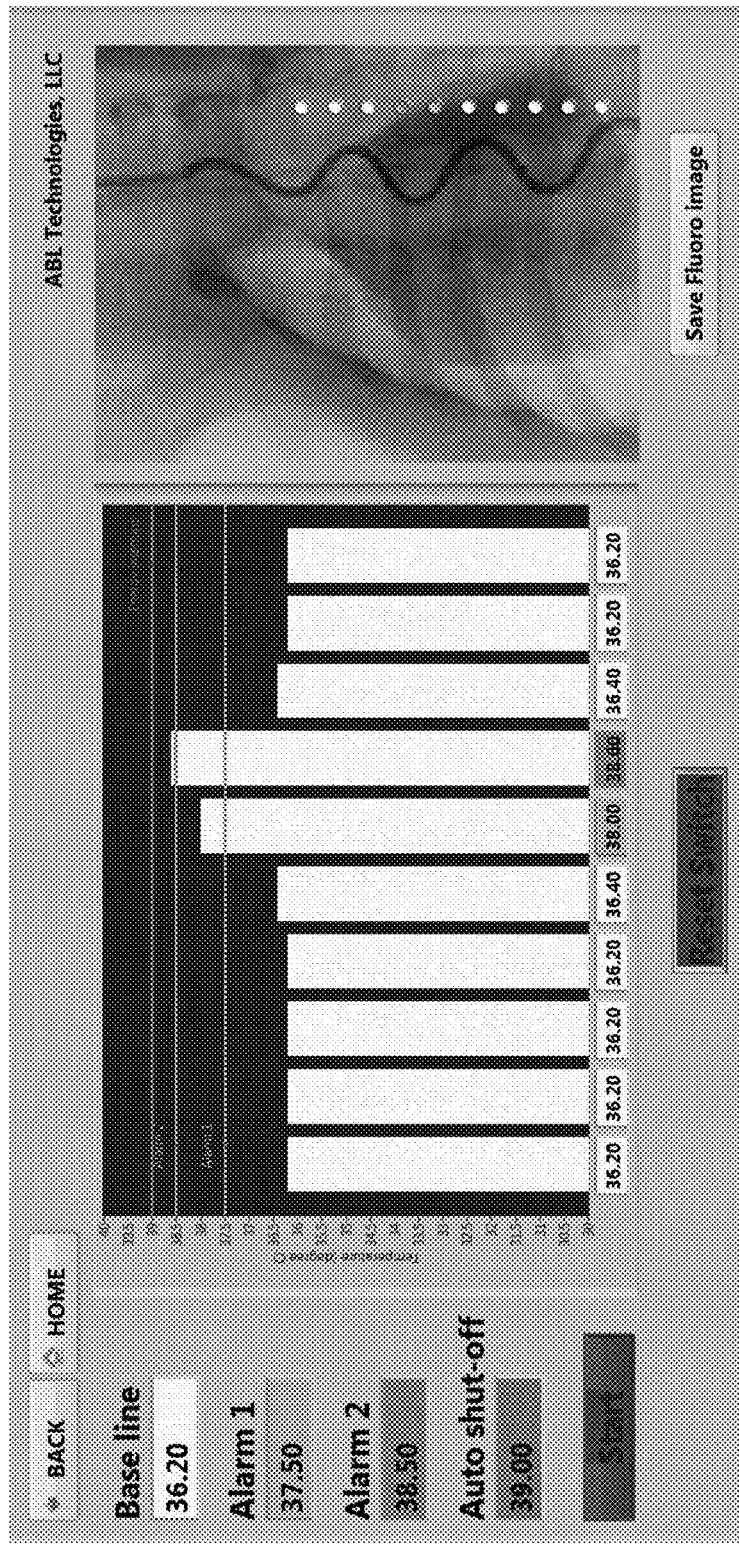
FIG. 15 is a picture of graphical unit interface (GUI) of the cardiac mapping system showing temperature readings from multiple sensors, as well as placement of multiple of the multiple sensors.

The graphical unit interphase (GUI) of applicant's cardiac mapping system of one embodiment is shown in FIG. 15. This esophageal temperature monitoring functionality and GUI is incorporated and integrated with other functions of the cardiac mapping system (or monitoring/recording system) such as "electro-antomical mapping".

The details of esophageal probe 414, connector box 400, cardiac mapping system 402, and ablation stopping box 404 are described below.

In one aspect of the disclosure, any esophageal temperature probe may be used. In one embodiment, the esophageal probe may have one thermistor or thermocouple (sensor). In another embodiment, the esophageal probe may have more than one thermistors (or thermocouples). These may comprise any number of thermistors (or thermocouples). Shown in FIG. 16 is an exemplary esophageal probe 406 that may be used. This esophageal probe has a number of thermistors 414. Various thermistors have conductor wires which travel through the body of the lumen 412, and are connected to terminal connector(s) 416. The terminal connector 416 (on the proximal end) of the esophageal probe 406 connects to a connector box 400 (FIGS. 13 and 14) to get sensor information into a cardiac mapping system 402 (or cardiac monitoring/recording system 403).

Figure 17B:
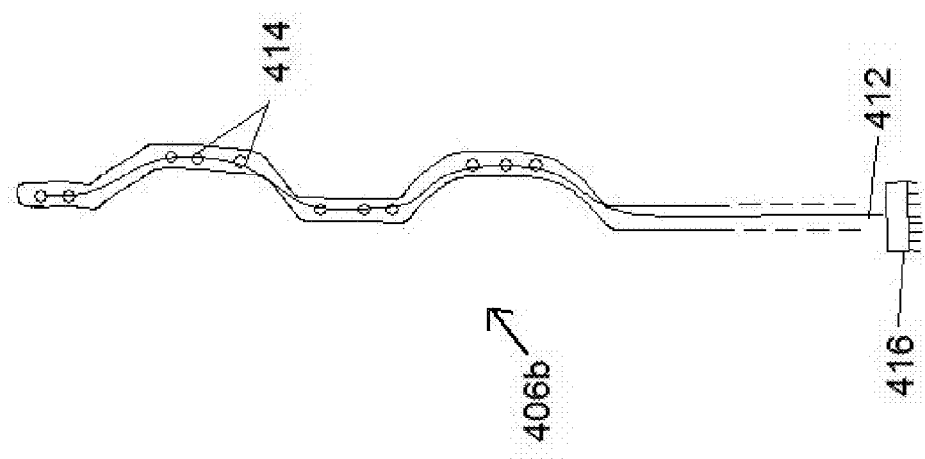
FIGS. 17A and 17B shows embodiments of esophageal probe that that are pre-formed.
Figure 17A:
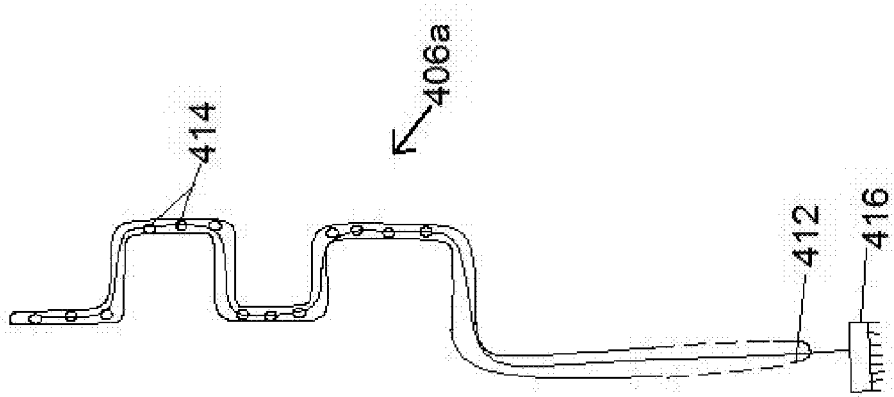

In one aspect of the disclosure, the esophageal probe 406a, 406b may have a pre-built memory or pre-defined shape. This pre-defined shape may be in the form of "S" shape or any other pre-built shape. Two examples (without limitation) of these shapes are shown in conjunction with FIG. 17A and FIG. 17B. The only thing different in this embodiment is the pre-defined (or pre-built) shape. The body or shaft of the esophageal probe 406, 406a, 406b may comprise a lumen or space for inserting a straight stylet. The straight stylet is used for straightening the esophageal probe for insertion and generally withdrawn after the placement of the esophageal probe in the esophagus 110. Same method of straightening the probe may be used to take the esophagus probe out.

In one embodiment, the esophageal probe 406 comprises an inflatable balloon, and the thermistor sensors are embedded in, or over the balloon. Examples of esophageal probe with inflatable balloon are shown in conjunction with FIGS. 18A and 18B. In the embodiment shown in FIG. 18A, the thermistors are encased in a covering of a sheath. In FIG. 18B, the thermistors are on top of the balloon and are exposed, giving the probe greater sensitivity and exposure. As previously stated, there may be any number of thermistors. The objective of the thermistors being on an inflatable balloon is that they will be in closer contact to the esophagus 110 wall for monitoring esophageal temperature.

The esophageal probe including the inflatable balloon comprising the thermistors may be enclosed in a sheath or membrane. This is shown in FIG. 19 where a sheath 418 is encased over the esophageal probe.

The connector box 400 (FIG. 13) houses the circuitry and is the interface between the esophageal probe 406 and the cardiac mapping system 402.

Figure 20:
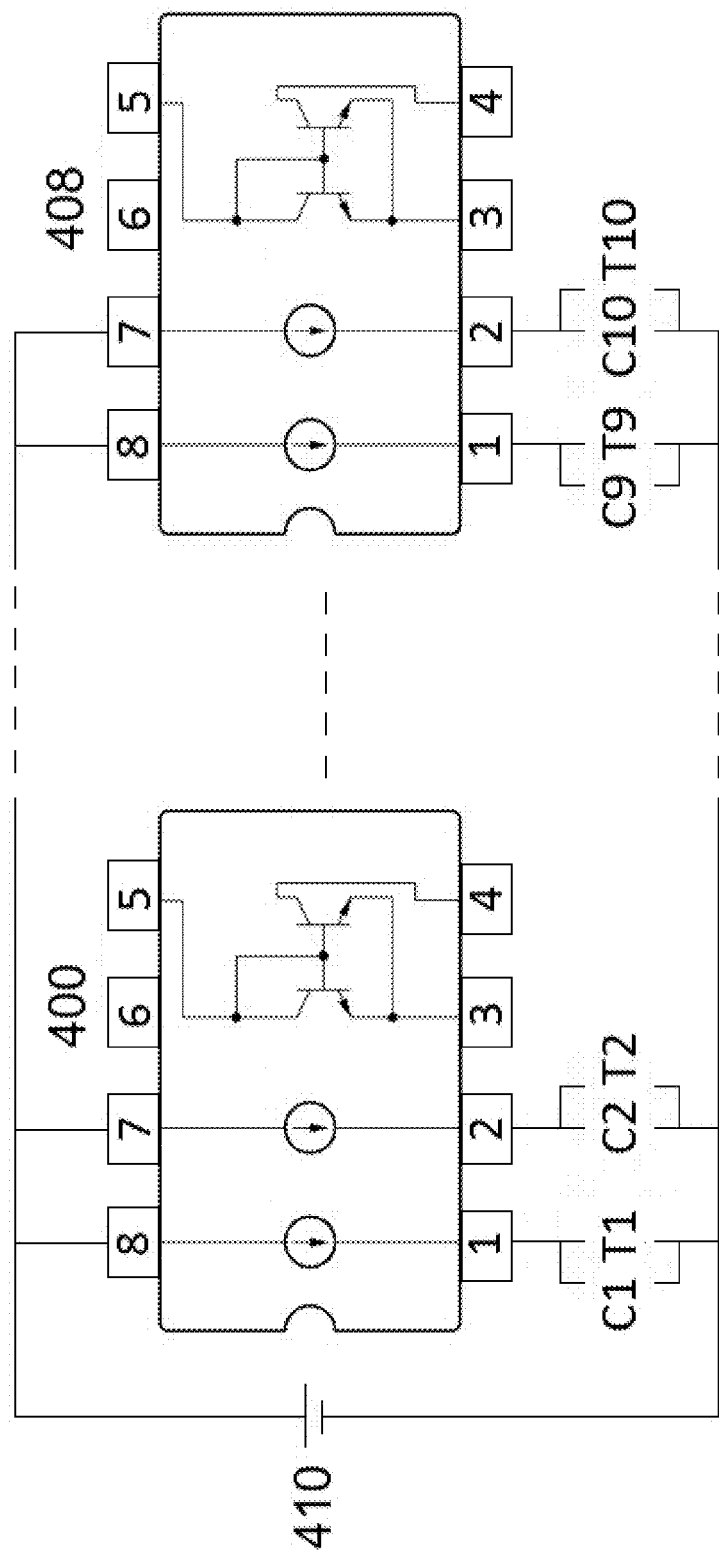
FIG. 20 shows an electrical diagram of circuitry for temperature measurements from ten thermistors.

Details of the circuitry are shown in conjunction with FIG. 20. To measure the temperature, ten of 2-wire thermistors are used (T1 to T10). Generally the thermistors are sensitive semiconductors in that their resistance varies with the temperature according to a linearized approximation. Also, thermistors generally have a fast response rate and their nominal resistance makes them the best option for precise measurements in lower-temperature applications like tissue temperatures while ablating (32 to 40° C.) for atrial fibrillation ablations.

Shown in conjunction with FIG. 20, to take temperature measurements, thermistors are supplied with current excitation source and the produced voltage across them (based on the ohms' law) is scaled into temperature by using the Steinhart-Hart thermistor third-order approximation as follow:

$$1/T = A + BR^{-1} + CR^{-3}$$

where T is the temperature in Kelvin, R is the thermistor's measured resistance, and A, B, and C are constants provided by the thermistor manufacturer.

Also, as shown in FIG. 20 in one embodiment for implementation of the excitation, five Texas Instruments Integrated Circuits called "REF200" (400 - - - 408) can be used. This 8-pin IC is a dual current source/current sink with three sections on a single chip. The three sections are two 100 µA current sources and a current mirror. Sections are dielectrically isolated which makes them completely independent. Since the current sources are two terminal devices, they can be used equally well as current sinks. The performance of each section is individually measured and laser-trimmed to achieve high accuracy at low cost. Pins 1 and 8 form the first 100 µA constant current source and pins 2 and 7 the second one. The current flows from pin 8 to 1 and from pin 7 to 2. Pins 3, 4 and 5 are also used for the current mirror. The sections can be pin-strapped for currents of 50 mA, 100 µA, 200 µA, 300 µA or 400 µA. External circuitry can be used to obtain virtually any current. Pin 6 is connected to a defined circuit potential to assure rated DC performance. The preferred connection is to the most negative constant potential in the system. In most analog systems this would be –VS. For best AC performance, pin 6 should be left open and unused sections unconnected. The IC can be powered from –6 V to +40 V (412).

Figure 21:
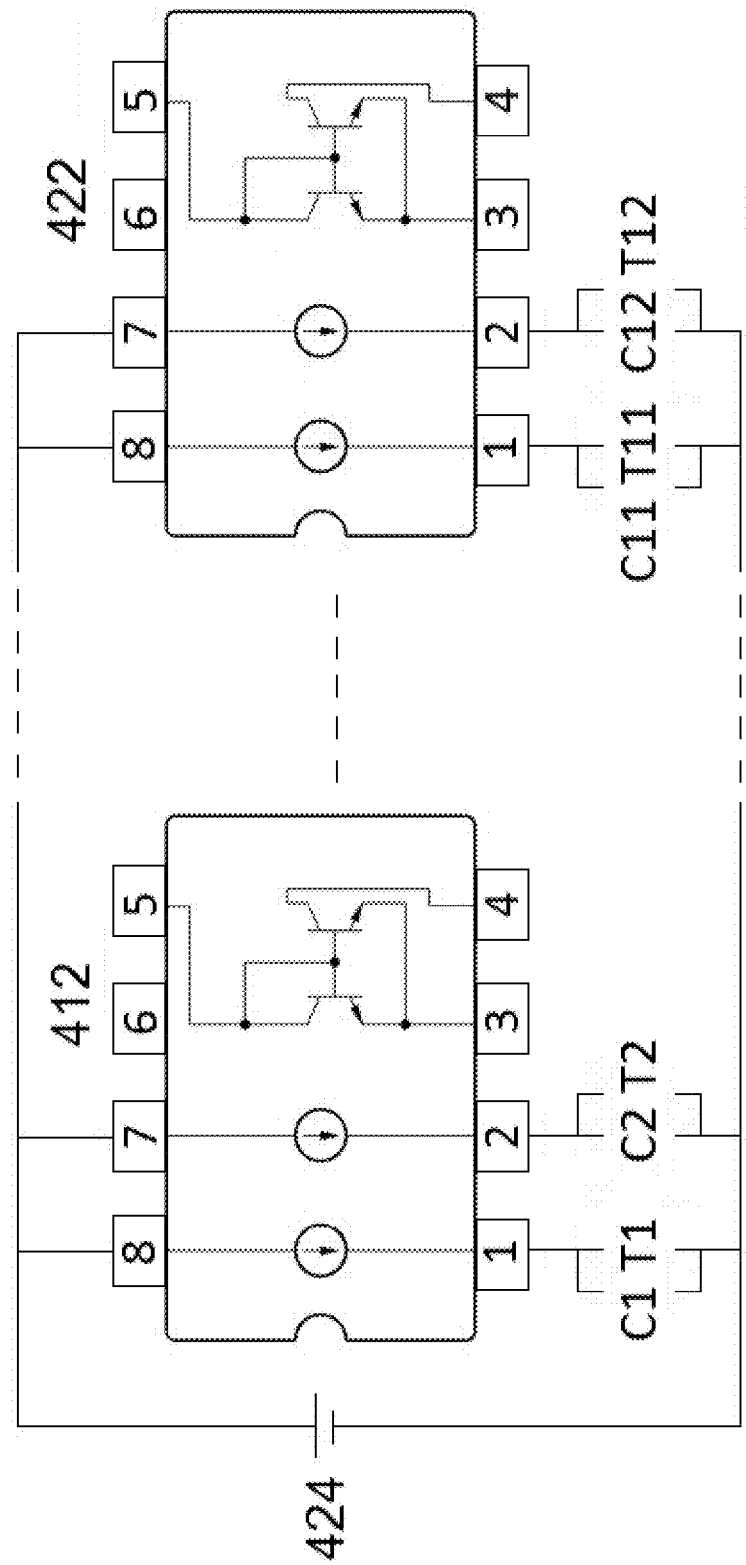
FIG. 21 shows an electrical diagram of circuitry for temperature measurements from twelve thermistors.

The voltages produced across the thermistors are acquired by an FPGA for reliable and continues real-time measurements (C1 to C12) and the voltage to temperature conversion is done in real-time by the system software. FIG. 21 shows an example of one implementation where six ICs are used for 12 thermisters on the esophageal probe.

Cardiac Mapping Systems

Cardiac mapping systems are well known in the art and are generally used during cardiac ablation procedure in atrial fibrillation procedures where temperature monitoring is needed.

The role of these mapping systems has been to keep a log of and make manageable and interpretable the vast amount of information obtained during an electrophysiology study. These systems have made possible the extensive intracardiac mapping that can now be performed and applied during electrophysiologic procedures. This enhanced mapping capability has been especially useful in the treatment of complex arrhythmias that require extensive ablation in the cardiac chambers, e.g., atrial fibrillation and ventricular arrhythmias.

The two of the commonly used mapping systems are CARTO (Biosense Webster) and NavX EnSite (St. Jude Medical, Inc.). CARTO uses a low-level magnetic field measured by a catheter location sensor, whereas NavX registers electrode impedance sensor in relation to skin patches that apply a low-level electrical current.

Electromagnetic Based Mapping System

Systems such as CARTO (Biosense Webster, Diamond Bar, Calif.) use the electromagnetic position of the catheter tip relative to an electromagnetic locator pad which is placed below the patient, and a reference catheter at a fixed external (usually posterior) location. The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of, a magnetic field emitter mounted under the patient; the external magnetic field emitter has 3 coils that generate ultra-low-intensity magnetic fields (between 5×10-6 and 5×10-5 T) that code the surrounding space with spatial information sensed by the field sensor at the tip of the mapping catheter a location sensor inside the mapping and ablation catheter tips, and a data processing unit and graphical display unit to generate and display the 3D model of the cardiac chamber of interest.

Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, pitch, and yaw. The position and orientation of the catheter tip can be seen on the screen and monitored in real-time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded red, orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Electrical Impedance Electroanatomic Mapping

The concept underlying the use of electrical impedance to calculate a spatial locations is based on the following: A very low-voltage alternating current of a particular localization frequency is applied across a patient's body using two skin electrodes confers a relatively linear voltage gradient across the tissues in the axis of the electrodes. The voltage can be detected by a sensing electrode and can then be converted to the axial location of the sensor. Three such orthogonal electric currents applied separately and detected by a sensor can thus be used to triangulate the 3-dimensional (3D) location of the sensor.

Mapping using this concept requires fulfillment of the following 4 conditions: 1) 3 orthogonal currents with the heart at the center need to be used to allow triangulation in 3-dimensional space; 2) the externally applied electric current should be easily detectable but benign to the patient and not interfere with the recorded electrograms; 3) the voltage gradient need to be calibrated to interpret recorded voltages for localization; and 4) spatial variations associated with the cardiac and respiratory cycles need to be accounted for. Thus stabilization of the whole localization apparatus throughout the mapping and ablation procedure is important to limit inaccuracies.

The EnSite NavX (St. Jude Medical, Inc. St. Paul, Minn.) was first described for electroanatomic mapping and navigation in atrial flutter ablation in 2004. A low electric current at 5.68 kHz is multiplexed with each of these pairs of electrodes to create the navigational electric field across the heart. A fixed intracardiac catheter (e.g., in the coronary sinus) or a surface electrode serves as the reference. The electrode position is averaged over 1 to 2 cardiac cycles to reduce cyclic cardiac variation. However, because of the long excursion of the respiratory cycle, eliminating respiratory variations by averaging becomes impossible without compromising the real-time localization and display.

Fluoroscopy Based Mapping System

In the method and system of fluoroscopy based mapping system, a cardiac mapping system has been disclosed where existing cardiac image or multiple images are utilized, and electrical parameter(s) information is/are superimposed on them to provide an "electro-anatomical" map. The existing cardiac image(s) may be a fluoroscope image or combined images such as a 3D computed tomography (CT) image overlayed or registered on a fluoroscope image, or other images as described later. This may also be referred to as a "sensor-less" cardiac mapping system, as the prior art systems comprise sensors that are impedance based or electromagnetic based, and the current disclosure describes a method and system that can perform electro-anatomical cardiac mapping without the impedance or electromagnetic based sensors.

Figure 22:
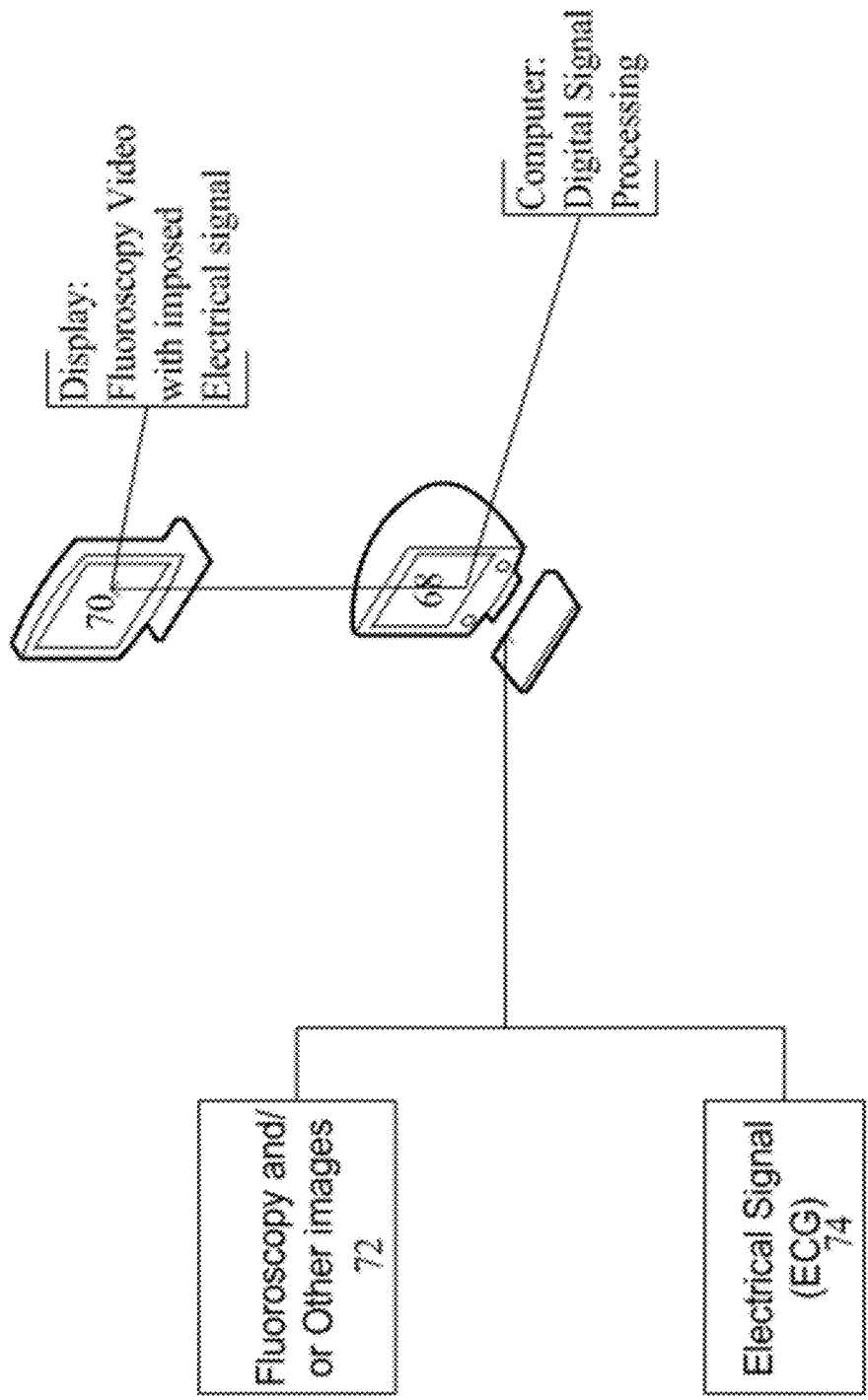
FIG. 22 is a block diagram showing energy interrupt for the procedure based on a command signal from a cardiac mapping (or cardiac monitoring/recording) system.

In the concept of this disclosure, a computer 68 is configured to receive multiple channels of electrical signals including 12-lead EKG and various intracardiac signals, shown in a simplified form in conjunction with FIG. 22. A computer, is generally a desktop workstation 68 (or a laptop 66—not shown) is configured to receive fluoroscopy 72 and/or other images into the computer 68. Additionally, there may be an output from the computer for feedback control of various things, for example interrupting energy delivery in certain situations. The interruption of energy delivery may be based on electrical signals and/or other parameters. One example would be interrupting energy delivery for AVNRT ablation based on timing relationships of the acquired atrial and ventricular signals. Another example would be interrupting ablation energy delivery based on esophageal temperature monitoring.

Ablation Stopping Box

Figure 23:
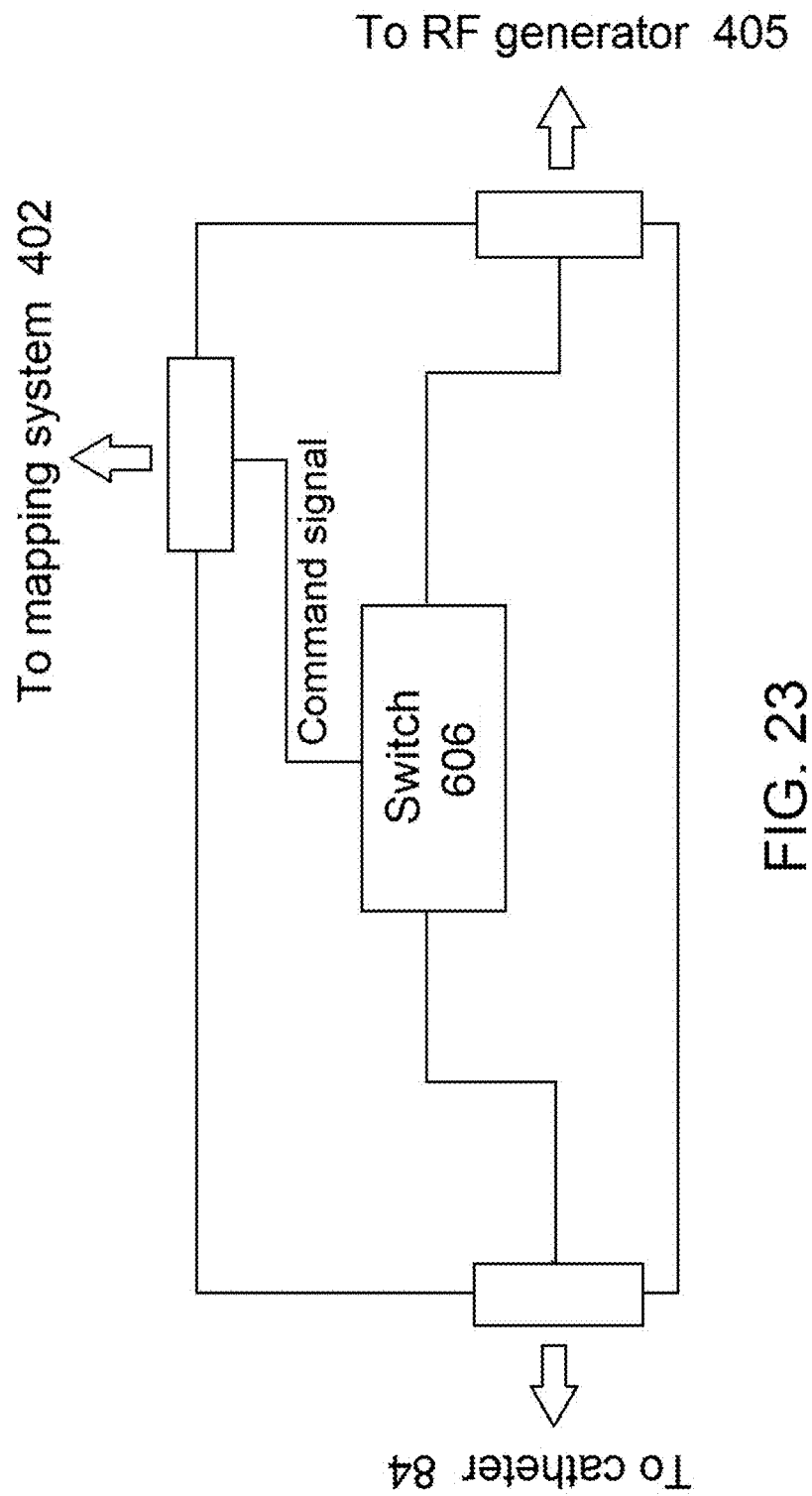
FIG. 23 shows electrical circuitry for energy interrupt (or stopping) of procedure based on temperature parameter(s) measurements.

The functioning of the stopping box is shown in conjunction with FIG. 23. The stopping box 404 is connected to the ablation catheter 84 on one end, an to the RF generator 602 on the other end. The stopping box 404 is also connected to the mapping system computer 402 (or cardiac monitoring/recording system 403). Based on meeting pre-determined criteria, selected by the physician or operator, the cardiac mapping system computer 402 sends a command signal to activate switch 606, to interrupt energy delivery to the ablation catheter 84.

Figure 24:
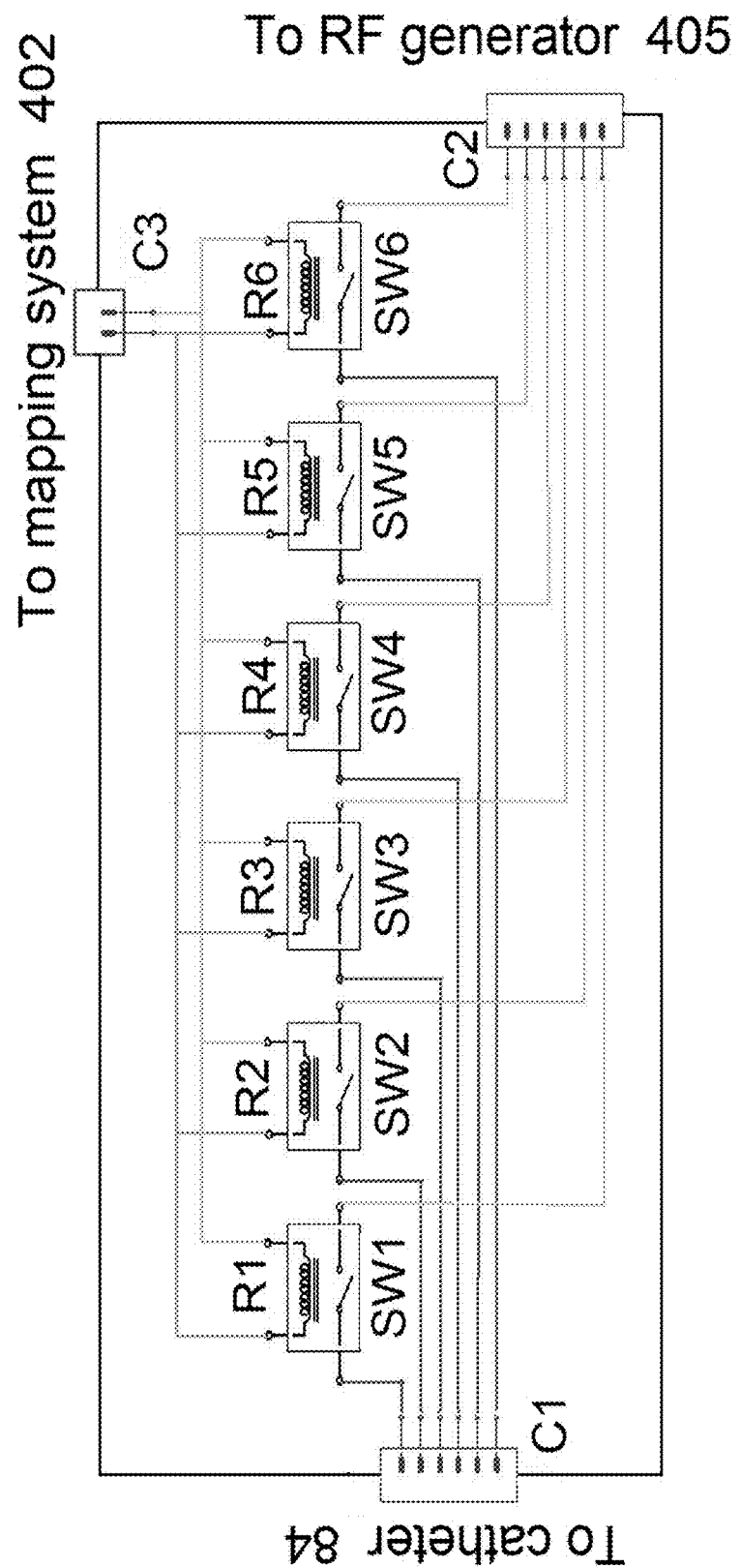
FIG. 24 shows implementation of electrical circuitry for energy interrupt (or stopping) of procedure based on temperature parameter(s) measurements.

In order to interrupt the RF energy delivery automatically during a procedure (based on pre-determined criteria) the system employs a stopping box 404. In one embodiment, the stopping box consists of six normally-closed DC voltage relay switches (SW1 to SW6) with 3 input/output connectors (C1 to C3). The schematic of the stopping box is shown in FIG. 24.

The numbers of relays are based on the specificity and brand of ablation catheter which goes to the patient's heart (600). In one embodiment two wires are used for measuring the temperature and the other four are for acquiring the intracardiac signals (from the distal pair and proximal pair). While ablating, one of the wires will conduct the RF signal from an RF signal generator instrument (602) and this wire is the one that is to be controlled by the stopping box for on-time energy interruption. The interruption command is generated from the mapping system (402).

Typically, the RF signal is 2 Watts with 0.5 Mega Hertz frequency and maximum 2 volts peak to peak voltage and 1 ampere electrical current. The rest of the signals are low voltage signals which barely exceed 1 volt. Thus, the relay switches should be able to tolerate the signals.

As mentioned earlier, we are just interested in interrupting the RF signal. But in order to prevent any unexpected damage to the RF generator instruments due to any current or voltage induction leakage via the returning wires, it is prudent to disconnect the whole path from the RF generator instrument and the ablation catheter by using six individual relay switches to be disconnected simultaneously. For this reason, as shown in FIG. 24, this embodiment has paralleled the relay part (R1 to R6) of all the switches and then connected to the mapping system (402). For the ease of implementing the design, we have used 6 identical relay switches with maximum RF signal tolerance.

The mapping system of this embodiment is able to provide 24 volt constant DC voltage for disconnecting the whole six relay switches simultaneously. Using DC voltage relay (instead of other switches like MOSFET transistors) generally increases the patient safety because in relay switches the coil part is completely isolated from the switch part and any unwanted frequency like the ones that harms the patient will not be transferred to the switch and won't mix the signals passing through. Additionally, in DC signals the harmful frequencies are already filtered.

Since the relay switches are normally closed, and after some processing and meeting some criteria in the mapping system they should open the circuit, there's no need for any impedance match between them and the ablation catheter 84 or RF generator 405.

The only important parameter in the switches (sw 1 to sw 6) is their closed state impedance which should be the minimum in order not to affect the ablation catheter working conditions.

The resetting process is done by the operator and by the absence of RF or any other signals and which makes the design simpler for other electrical issues.

The stopping box will be an interface between the ablation catheter and the RF generator instrument. So, regardless of the number of the wires used for the ablating process, the connectors on the stopping box where it is connected to the catheter and the RF generator should match the proper ones. These connectors could be two 14 pin female REDEL connectors on two opposite sides of the box corresponding to the color of the connectors on the catheter and the RF generator (C1 and C2). The other 2 pin connector which delivers the 24 volts DC voltage from the mapping system (C3), could be any reliable connector used for medical applications.

Use with Cryoablations

It will be clear to one skilled in the art, that the temperature monitoring system may be used for both radiofrequency (RF) ablations and cryoablations. In RF ablations the concern is injury due to heating. In cryoablation, the concern is injury due to cooling. In Cryoablation the temperatures are typically brought to −40° C. Potentially, the injury due to freezing could be carried over to the esophagus. In this embodiment, the alarm(s) and/or interrupt are due to reaching the limit of the decrease in temperature as opposed to increase in temperature in RF ablation. In either case, the intent is to avoid or minimize the injury to the esophagus.

Cryotheraphy or use of cold temperatures to elicit a specific tissue response, has a history of effective medical use and cryoablation systems are also used routinely for atrial fibrillation ablations. The ultimate purpose of cryoablation is to freeze tissue in a discrete and focused fashion to destroy cells in a precisely targeted area. The application of cryothermal energy results in the formation of an ice ball. Cooling first occurs at the distal catheter tip in contact with endocardial tissue. Freezing then extends radially into the tissue, establishing a temperature gradient. The lowest temperature and fastest freezing rate are generated at the point of contact, with slower tissue cooling rates at the peripheral regions. The mechanism of tissue damage are complex and still debated, but involve freezing and thawing, hemorrhage and inflammation, replacement fibrosis, and apoptosis.

Generally in cryoablations tissue hypothermia causes cardiomyocytes to become less fluidic as metabolism slows, the ion pumps to lose transport capabilities, and the intracellular pH to become more acidic. These effects may be transient, depending on the interplay between temperature and duration. The shorter the exposure to a hypothermic insult and/or the warmer the temperature, the faster the cells recover. As a clinical correlate, this characteristic feature of cryoenergy permits functional assessment of putative ablation sites (i.e., cryomapping) without cellular destruction.

By contrast, the hallmark of permanent tissue injury induced by hypothermia is formation of ice crystal. As cells are rapidly cooled to freezing temperatures, ice crystals are first formed within the extracellular matrix, and then formed intracellularly. The size of ice crystals and their density are dependent on the combination of the following proximity to the cryoenergy source, the local tissue temperature achieved, and the rate of freezing, initially, ice crystals are formed exclusively in the extracelluar space as the tissue temperature drops below −150 C. Progressive cooling to below −400 C results in the formation of intracellular ice crystals in the extracelluar space results in it becoming relative hypertonic. In an attempt to reestablish osmotic equilibrium, there is a compensatory egress of water from the intracellular to the extracellular space, with subsequent cellular shrinkage, resulting in intracellular desiccation Further, the newly established osmotic gradient precipitates a diffusion gradient between extracellusr and intracellular spaces, resulting in the net movement of H+ inos out of the cell, and the migration of solute ions into the cell. Concomitant increase in the intracellular saline concentration with a reduction in tntracellular pH results in cellular protein damage, enzyme system impairment, and adverse effects on lipoprotein components of the plasma membrane. Of all the cytoplasmic components, the mitochondria are particularly sensitive and are the first structures to sufer irreversible damage.

Upon completion of the freezing phase, the tissue passively returns to body temperature resulting in a thawing effect. This second phase induces cellular damage through a combination of two mechanisms. First, recrystallization and coalescence of intracellular and extracellular ice crystals increase the osmotic damage and generate shear forces, which further disrupt tissue architecture. Second, restoration of microcirulatory function is associated with a hyperemic vascular response characterized by hemorrhage and inflammation (co-agulation necrossis). Specifically, blood vessel walls become porous leading to increased capillary permeability and subsequent interstitial edema. This vascular congestion, combined iwht endothelial injury induces platelet aggregation and microthrombi formation, and culminates in vascular obliteration and ischemic cellular necrosis. As such, while the central region subjected to the coldest freezing temperature undergoes direct cellular damage, the surrounding microvascular injury results in the extension of tissue destruction.

The final phase of cryoinjury begins concurrent to thawing and is characterized by reactive inflammation, followed by tissue repair and replacement fibrosis. Over the subsequent weeks, these processes culminate in the generation of a mature lesion, which has a distinct, well-circumscribed central region of dense fibrosis surrounded by a narrow border zone of viable cellular death (due to microvacular injury and apoptosis).

Generally, a cryocatheter consists of a hollow shaft with a closed distal end containing a cooling electrode tip, integrated thermocouple deice and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gasphase change results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −300 C for a maximum of 80 seconds so as to prevent irreversible tissue damage. The second mode is cryoablation, which results in cooling of the catheter tip to at leat −750 C for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

One of the most exciting and truly remarkable characteristics of cryothermal energy is the ability to dynamically and prospectively asses the ability to safety and efficacy of a potential ablation lesion site, because a period of reversible electrophysiologic tissue inhibition obligatorily precedes permanent tissue destruction (a process that that can be dynamically manipulated by varying the temperature and/or time of application). While extreme freezing (i.e., tissue temperature colder than −50° C.) results in near instantaneous permanent tissue injury, a functional effect may be obtained at some lethal temperatures (i.e., −10° C. to −25° C.), but complete recovery of all electrophysiologic properties and no histologically identifiable damage. Prior mapping is not theoretically possible, but the broad temperature/time window between reversible and irreversible effects renders this feature readily clinically applicable. This by identifying the desired substrate before definitive ablation, the appropriate catheter placement site may be confirm to be efficacious (i.e., efficacy curo mapping) and/or safe i.e., safety cyro mapping). Reversible cyro mapping may be of particular importance when ablating with myogenic substrates located near critical sites such as the AV node, where images target lesion may have major consequences. Reversibility observed with cryotherapy oh energy contrasts starkly with RF energy. With RF ablations, hydrothermal tissue energy leading to reversible loss of excitability occurs at a median tissue temperature of 48° C., as reversible tissue destruction occurs at tissue temperatures greater than 50° C. The reversibility window is, therefore, too narrow for safe clinical applications.

Advantages of cryoablations include,

Catheter Stability

Hyperthermia generated at the distal cooling electrode, the trial catheter adheres to tissue affording greater catheter stability. Metaphorically, this has been likened to a better tongue sticking to a frozen pole. The operator may let go of the catheter once it is adhered onto the endocardial surface. The programmed electrical stimulation may be performed during cryoablation without concern for catheter dislodgemeant. Moreover brushing effects that occurred during beat-to-beat rocketing heart motions and with respiratory variations are eliminated Minimal Risk of Thromboembolism To compare the propensity for RF and Pyo ablation to produce hot thrombus on the surface of the ablation lesion, it randomize preclinical study was conducted involving 197 ablation lesions in 22 dogs at right atrial, right front, left ventricular sites RF energy was five times more thermogenic than cryoablation, as confirmed by results of historical morphometric analysis seven days after ablation moreover, thrombus volume was significantly greater with RF compared with cryoablation. Interestingly the extent of IPO thermic injury was positively correlated with thrombus spoke. This was unlike bioenergy, in which lesion that mentions for not predictive of thrombus ice.

Moreover, cryothermal ablation lesions are associated with a lesser degree of platelet and coagulation cascade activation when compared with RFCA.

Minimal Risk to Vascular Structures

Concerns have been raised regarding RF ablation adjacent to or within coronary venous system or TVs, with venous injury (including acute perforation and Tampa not, and/or delayed fibrosis/stenosis), acute or sub acute and/or luminal venous thrombosis, and collateral damage to the esophagus and/or adjacent coronary arteries being reported. Perforation, or not, and coronary artery stenosis are potential complications. The circumflex and/or coronary artery may course in close proximity to the arrhythmia substrate. Moreover, the AV node oh artery passes near the mouth of the coronary sinus, the ablation may conceivably damage this vessel. Preclinical studies suggest a lower incidence of coronary artery stenosis following cryoablation compared with RF ablation.

Painless Ablation

RF ablation may be painful to the patient under conscious sedation through direct stimulation of cardiac sensory nerves or pericardial or collateral Whisler visceral irritation, particularly when ablating your thin-walled or venous structures such as posterior left atrium, coronary sinus, or posterior cable tricuspid Isthmus. In contrast to our FCA, several studies have noted that again perception, as assessed by standard Likert scale, is significantly less with cryoablation. This first select procedures associated with substantial patient discomfort, the use of cryoablation may theoretically result in lower anesthetic and analgesic requirements. This is especially relevant for electrophysiology laboratories that do not use general anesthesia. However, it should be noted that in the case of AF ablation, a rare incidence of transient ice cream headache has been described during ablation.

Visualization by Ultrasound

In the 1990s, the ability to provide continuous real-time imaging of the freezing process was considered a major technological advancement that sparked renewed interest in visceral cryosurgery. Indeed, ultrasonographic monitoring of the freeze-thaw cycle and frozen tissue volume contributed to rapid improvements in hepatic and prostatic surgery. The ability to visualize formation of ice ball by ultrasonic means was likewise demonstrated in preclinical transcatheter cryoablation studies. This feature of cryoablation has proved helpful in defining optimal freezing parameters.

While this diclosure has been described with reference to preferred embodiments, it will be understood by those skilled in the art that various changes may be made without departing from the scope of the invention. In addition, many modifications may be made to adapt a particular situation or material to the teaching of the invention with departing from the essential scope thereof. Therefore, it is intended that the disclosure not be limited to the particular embodiments disclosed for carrying out this invention, but that the invention will include all embodiments falling within the scope of the appended claims.

The invention claimed is:

1. A method of activating alarms and/or interrupting or pausing energy delivery during an atrial fibrillation ablation procedures, comprises:
   placing a temperature probe in the esophagus of a patient, wherein said temperature probe comprises more than one temperature sensing members on said probe;
   providing information from said temperature sensing member into a electrophysiology monitoring/recording system or a cardiac mapping system via an interface electronics wherein, said cardiac monitoring/recording system or the cardiac mapping system comprises software configured and programmed for detecting at least one predetermined event(s) based on temperature parameter(s) levels of said at least one sensing member, and capable of interrupting or pausing energy delivery for said ablation;
   defining limits of said at least one predetermined event(s), wherein said at least one predetermined event(s) comprises an operator selected pre determined esophageal temperature parameter level(s);

detecting said at least one predetermined event(s) by the system wherein said predetermined event is based on the highest or lowest temperature parameter from any one of said temperature sensing members; and interrupting or pausing ablation energy delivery based on a command signal from said electrophysiology monitoring/recording system or a cardiac mapping system via said interface electronics wherein, said interface electronics is configured and adapted to bring in said temperature parameter(s) levels into said electrophysiology monitoring/recording system or a cardiac mapping system, and for interrupting or pausing energy delivery for said ablation.

2. The method of claim 1, wherein energy delivery interrupt means comprises a relay switch or an alternate device capable of interrupting the ablation energy circuit.

3. The method of claim 1, wherein said electrophysiology monitoring/recording system may be one of GE's CardioLab® system, St Jude's EP Workmate® systems, CR Bard's LabSystem™ PRO, or any FDA approved cardiac monitoring/recording system, and said cardiac mapping system may be one of Biosense Webster's Carton™ mapping system, St Jude Medical's Navix™/Velocity™ mapping system, mapping system available from Rhythmia Medical/Boston Scientific, or any FDA approved cardiac mapping system.

4. The method of claim 1, wherein software may be one from a group comprising LAB WINDOWS/CVI, LABVIEW (National Instruments Corp.), C, C+, Microsoft Visual C++, Dot Net framework, MATLAB, and Microsoft Visual Basic, or any functional equivalent software language.

5. The method of claim 1, wherein said predetermined event(s) is an elevated temperature level and/or rate of change of temperature or a decrease in esophageal temperature level.

6. The method of claim 1, wherein said ablation may be radiofrequency (RF) or cryoablation.

7. The method of claim 1, wherein said esophageal probe may comprise thermistor or thermocouple for measuring temperature.

8. The method of claim 1, wherein said esophageal probe may have a preformed shape.

9. A system for activating alarm(s) and/or interrupting energy delivery during a cardiac ablation procedure, comprises:

an esophageal temperature probe with more than one temperature sensing members;

an interface electronics for providing information from said temperature sensing member(s) into a cardiac monitoring/recording system or a cardiac mapping system;

said cardiac monitoring/recording system or a cardiac mapping system configured and programmable for detecting at least one predetermined event(s) based on temperature parameter(s) levels of said at least one sensing member and capable of activating alarm(s) and/or interrupt or pause energy delivery for said ablation; and means for activating alarms and/or interrupt or pause energy delivery based on pre-determined temperature wherein, said activating alarms and/or interrupt or pause of energy delivery is based on a command signal from said electrophysiology monitoring/recording system or a cardiac mapping system and wherein, said interface electronics is also used for interrupt or pause of energy delivery for said ablation procedure.

10. The system of claim 9, wherein said electrophysiology/monitoring/recording system can be one of GE's CardioLab® system, St Jude's EP Workmate® systems, CR Bard's LabSystem™ PRO, or any FDA approved cardiac monitoring/recording system, and said cardiac mapping system which can be one of Biosense Webster's Carton™ mapping system, St Jude Medical's Navix™/Velocity™ mapping system, mapping system available from Rhythmia Medical/Boston Scientific, or any FDA approved cardiac mapping system.

11. The system of claim 9, wherein energy delivery interrupt means comprises a relay switch or an alternate device capable of interrupting the ablation energy circuit.

12. The system of claim 9, wherein software may be one from a group comprising LAB WINDOWS/CVI, LABVIEW (National Instruments Corp.), C, C+, Microsoft Visual C++, Dot Net framework, MATLAB, and Microsoft Visual Basic, or any functional equivalent software language.

13. The system of claim 9, wherein said predetermined event(s) is an elevated temperature level and/or rate of change of temperature or a decrease in esophageal temperature level.

14. The system of claim 9, wherein said ablation may be radiofrequency (RF) or cryoablation.

15. The system of claim 9, wherein said esophageal probe may have a preformed shape.

16. A system for activating alarm(s) and/or interrupting energy delivery during a cardiac ablation procedure, comprises:

an esophageal temperature probe wherein said temperature probe comprises one or more locations on said probe for sensing temperature;

a computer based system comprising a processor and software configured and programmed for detecting at least one pre-determined esophageal temperature parameter level(s) selectable by an operator, and capable of initiating alarm(s) and/or energy delivery interrupt, based on reaching said at least one pre-determined level(s) of temperature parameter(s) of said esophageal temperature probe, wherein said computer based system is part of a cardiac monitoring/recording system which may be one of one of GE's CardioLab® system, St Jude's EP Workmate® systems, CR Bard's LabSystem™ PRO, or any FDA approved cardiac monitoring/recording system; and energy delivery interrupt means for activating alarms and/or energy delivery interrupt based on reaching pre-determined temperature parameters which is based on a command signal from said cardiac monitoring/recording system.

17. The system of claim 16, wherein said energy delivery interrupt means comprises a relay switch or an alternate device capable of interrupting the ablation energy circuit.

18. The system of claim 16, wherein said energy delivery interrupt is via an ablation stopping box receiving command from said computer, and connected to the ablation catheter.

19. The system of claim 16, wherein said predetermined event(s) is an increase or decrease in temperature level and/or rate of change of temperature.

20. The system of claim 16, wherein said esophageal probe may have a preformed shape.

* * * * *